United States Patent
Ryan et al.

(10) Patent No.: US 9,615,949 B2
(45) Date of Patent: Apr. 11, 2017

(54) DELIVERY DEVICE

(75) Inventors: Michael Ryan, Limerick (IE); Donagh O'Sullivan, Castleroy (IE); Fionan Keady, Glenamaddy (IE)

(73) Assignee: Cook Medical Technologies LLC, Bloomington, IN (US)

( * ) Notice: Subject to any disclaimer, the term of this patent is extended or adjusted under 35 U.S.C. 154(b) by 1105 days.

(21) Appl. No.: 12/649,046

(22) Filed: Dec. 29, 2009

(65) Prior Publication Data

US 2010/0168834 A1 Jul. 1, 2010

Related U.S. Application Data

(60) Provisional application No. 61/141,455, filed on Dec. 30, 2008.

(51) Int. Cl.
*A61F 2/95* (2013.01)
*A61F 2/966* (2013.01)

(52) U.S. Cl.
CPC .......... *A61F 2/95* (2013.01); *A61F 2/966* (2013.01); *A61F 2002/9511* (2013.01); *A61F 2002/9517* (2013.01); *A61F 2002/9534* (2013.01)

(58) Field of Classification Search
CPC .... A61F 2/95; A61F 2/966; A61F 2002/9517; A61F 2002/9534; A61F 2002/9511; A61F 2002/9522; A61M 25/005
USPC .............. 623/1.11, 1.12, 1.23; 606/108
See application file for complete search history.

(56) References Cited

U.S. PATENT DOCUMENTS

| | | | |
|---|---|---|---|
| 1,724,983 | A | 8/1929 | Weiss |
| 3,132,549 | A | 5/1964 | Lee |
| 3,888,258 | A | 6/1975 | Akiyama |
| 3,897,786 | A | 8/1975 | Garnett et al. |
| 4,559,041 | A | 12/1985 | Razi |
| 4,655,771 | A | 4/1987 | Wallsten |

(Continued)

FOREIGN PATENT DOCUMENTS

| | | |
|---|---|---|
| CA | 2739275 A1 | 4/2010 |
| EP | 566 807 A1 | 10/1993 |

(Continued)

OTHER PUBLICATIONS

International Search Report for International Application No. PCT/US2009/069721 mailed Feb. 19, 2010.

(Continued)

*Primary Examiner* — Katherine Rodjom
(74) *Attorney, Agent, or Firm* — Brinks Gilson & Lione

(57) ABSTRACT

A delivery device for deploying an expandable prosthesis and method of use thereof are described. The delivery device includes an outer sheath that is capable of retracting in a proximal direction and resheathing over the prosthesis in a distal direction. The device includes a drive pulley that can engage gears to retract or resheath the outer catheter in relation to the prosthesis. In some embodiments, the delivery device may include a reinforced outer sheath disposed over an inner elongate member, the reinforced outer sheath comprising a proximal section reinforced with a braid, a distal section reinforced with a coil and an overlapping section extending between the proximal section and the distal section. Additionally or alternatively, the delivery device may include a stabilizing element for releasably holding the stent to the inner catheter.

19 Claims, 30 Drawing Sheets

(56) References Cited

U.S. PATENT DOCUMENTS

| | | | |
|---|---|---|---|
| 4,921,484 A | 5/1990 | Hillstead | |
| 5,026,377 A | 6/1991 | Burton et al. | |
| 5,275,151 A | 1/1994 | Shockey et al. | |
| 5,372,600 A | 12/1994 | Beyar et al. | |
| 5,415,664 A | 5/1995 | Pinchuk | |
| 5,433,723 A | 7/1995 | Lindenberg et al. | |
| 5,443,477 A | 8/1995 | Marin et al. | |
| 5,458,615 A | 10/1995 | Marin et al. | |
| 5,554,894 A | 9/1996 | Sepielli | |
| 5,681,323 A | 10/1997 | Arick | |
| 5,683,451 A | 11/1997 | Lenker et al. | |
| 5,690,644 A | 11/1997 | Yurek et al. | |
| 5,700,269 A | 12/1997 | Pinchuk et al. | |
| 5,702,373 A * | 12/1997 | Samson | 604/527 |
| 5,702,418 A | 12/1997 | Ravenscroft | |
| 5,707,376 A | 1/1998 | Kavteladze et al. | |
| 5,709,703 A | 1/1998 | Lukic et al. | |
| 5,733,325 A | 3/1998 | Robinson et al. | |
| 5,759,186 A | 6/1998 | Bachmann et al. | |
| 5,776,142 A | 7/1998 | Gunderson | |
| 5,833,694 A | 11/1998 | Poncet | |
| 5,906,619 A | 5/1999 | Olson et al. | |
| 5,944,727 A | 8/1999 | Ahari et al. | |
| 5,968,052 A | 10/1999 | Sullivan, III et al. | |
| 5,993,460 A | 11/1999 | Beitelia et al. | |
| 6,093,194 A | 7/2000 | Mikus et al. | |
| 6,146,415 A | 11/2000 | Fitz | |
| 6,162,231 A | 12/2000 | Mikus et al. | |
| 6,168,610 B1 | 1/2001 | Marin et al. | |
| 6,238,402 B1 | 5/2001 | Sullivan, III et al. | |
| 6,254,628 B1 | 7/2001 | Wallace et al. | |
| 6,270,520 B1 * | 8/2001 | Inoue | A61F 2/07 623/1.11 |
| 6,346,118 B1 | 2/2002 | Baker et al. | |
| 6,375,676 B1 | 4/2002 | Cox | |
| 6,383,211 B1 | 5/2002 | Stachle | |
| 6,391,050 B1 | 5/2002 | Broome | |
| 6,391,051 B2 | 5/2002 | Sullivan, III et al. | |
| 6,402,760 B1 | 6/2002 | Fedida | |
| 6,413,269 B1 | 7/2002 | Bui et al. | |
| 6,428,566 B1 | 8/2002 | Holt | |
| 6,514,261 B1 | 2/2003 | Randall et al. | |
| 6,520,983 B1 | 2/2003 | Colgan et al. | |
| 6,530,949 B2 | 3/2003 | Konya et al. | |
| 6,592,549 B2 | 7/2003 | Gerdts et al. | |
| 6,599,296 B1 | 7/2003 | Gillick et al. | |
| 6,629,981 B2 | 10/2003 | Bui et al. | |
| 6,669,719 B2 | 12/2003 | Wallace et al. | |
| 6,673,101 B1 | 1/2004 | Fitzgerald et al. | |
| 6,695,862 B2 | 2/2004 | Cox et al. | |
| 6,695,875 B2 | 2/2004 | Stelter et al. | |
| 6,749,627 B2 | 6/2004 | Thompson et al. | |
| 6,755,854 B2 | 6/2004 | Gillick et al. | |
| 6,755,855 B2 | 6/2004 | Yurek et al. | |
| 6,786,918 B1 | 9/2004 | Krivoruchko et al. | |
| 6,808,529 B2 | 10/2004 | Fulkerson | |
| 6,821,291 B2 | 11/2004 | Bolea et al. | |
| 6,860,898 B2 | 3/2005 | Stack et al. | |
| 6,866,669 B2 | 3/2005 | Buzzard et al. | |
| 6,890,317 B2 | 5/2005 | Gerdts et al. | |
| 6,893,458 B2 | 5/2005 | Cox et al. | |
| 6,911,039 B2 | 6/2005 | Shiu et al. | |
| 6,926,732 B2 | 8/2005 | Derus et al. | |
| 6,939,352 B2 | 9/2005 | Buzzard et al. | |
| 6,942,688 B2 | 9/2005 | Bartholf et al. | |
| 6,991,646 B2 | 1/2006 | Clerc et al. | |
| 7,052,511 B2 | 5/2006 | Weldon et al. | |
| 7,122,058 B2 | 10/2006 | Levine et al. | |
| 7,335,224 B2 | 2/2008 | Øhlenschlæger | |
| 2002/0007206 A1 | 1/2002 | Bui et al. | |
| 2002/0095203 A1 | 7/2002 | Thompson et al. | |
| 2002/0111666 A1 | 8/2002 | Hart et al. | |
| 2002/0183827 A1 | 12/2002 | Derus et al. | |
| 2003/0093084 A1 | 5/2003 | Nissan et al. | |
| 2003/0135162 A1 * | 7/2003 | Deyette et al. | 604/236 |
| 2003/0144671 A1 | 7/2003 | Brooks et al. | |
| 2003/0191516 A1 | 10/2003 | Weldon et al. | |
| 2003/0225445 A1 | 12/2003 | Derus et al. | |
| 2004/0006380 A1 | 1/2004 | Buck et al. | |
| 2004/0010265 A1 | 1/2004 | Karpiel | |
| 2004/0093057 A1 | 5/2004 | Bolduc et al. | |
| 2004/0181239 A1 | 9/2004 | Dorn et al. | |
| 2004/0186547 A1 | 9/2004 | Dorn et al. | |
| 2004/0193180 A1 | 9/2004 | Buzzard et al. | |
| 2004/0215229 A1 | 10/2004 | Coyle | |
| 2004/0220653 A1 | 11/2004 | Borg et al. | |
| 2004/0267282 A1 | 12/2004 | Shkarubo et al. | |
| 2005/0021123 A1 | 1/2005 | Dorn et al. | |
| 2005/0033402 A1 | 2/2005 | Cully et al. | |
| 2005/0033403 A1 | 2/2005 | Ward et al. | |
| 2005/0060016 A1 | 3/2005 | Wu et al. | |
| 2005/0060018 A1 | 3/2005 | Dittman | |
| 2005/0080476 A1 | 4/2005 | Gunderson et al. | |
| 2005/0085890 A1 | 4/2005 | Rasmussen et al. | |
| 2005/0090834 A1 | 4/2005 | Chiang et al. | |
| 2005/0090890 A1 | 4/2005 | Wu et al. | |
| 2005/0107862 A1 * | 5/2005 | Ohlenschlaeger | 623/1.11 |
| 2005/0113902 A1 | 5/2005 | Geiser et al. | |
| 2005/0131514 A1 | 6/2005 | Hijikema et al. | |
| 2005/0149159 A1 | 7/2005 | Andreas et al. | |
| 2005/0177246 A1 | 8/2005 | Datta et al. | |
| 2005/0182475 A1 | 8/2005 | Jen et al. | |
| 2005/0209670 A1 | 9/2005 | George et al. | |
| 2005/0209685 A1 | 9/2005 | Shifrin et al. | |
| 2005/0240254 A1 | 10/2005 | Austin | |
| 2005/0256562 A1 | 11/2005 | Clerc et al. | |
| 2005/0273151 A1 | 12/2005 | Fulkerson et al. | |
| 2005/0288763 A1 | 12/2005 | Andreas et al. | |
| 2005/0288764 A1 | 12/2005 | Snow et al. | |
| 2005/0288766 A1 | 12/2005 | Plain et al. | |
| 2006/0004433 A1 | 1/2006 | Greenberg et al. | |
| 2006/0009858 A1 | 1/2006 | Levine et al. | |
| 2006/0184224 A1 | 8/2006 | Angel | |
| 2006/0184226 A1 | 8/2006 | Austin | |
| 2007/0060996 A1 * | 3/2007 | Goodin et al. | 623/1.11 |
| 2007/0060999 A1 * | 3/2007 | Randall et al. | 623/1.11 |
| 2007/0219614 A1 * | 9/2007 | Hartley | 623/1.11 |
| 2007/0270779 A1 * | 11/2007 | Jacobs | A61M 25/0045 604/525 |
| 2008/0188920 A1 * | 8/2008 | Moberg et al. | 623/1.12 |
| 2008/0300613 A1 * | 12/2008 | Shelton et al. | 606/170 |
| 2009/0024133 A1 | 1/2009 | Keady et al. | |
| 2009/0030497 A1 | 1/2009 | Metcalf et al. | |
| 2009/0099640 A1 | 4/2009 | Weng | |
| 2010/0049168 A1 * | 2/2010 | Parker et al. | 604/527 |
| 2010/0262157 A1 | 10/2010 | Silver et al. | |
| 2011/0190865 A1 | 8/2011 | McHugo et al. | |
| 2012/0172963 A1 | 7/2012 | Ryan et al. | |
| 2012/0185031 A1 | 7/2012 | Ryan et al. | |
| 2012/0221093 A1 | 8/2012 | McHugo | |

FOREIGN PATENT DOCUMENTS

| | | |
|---|---|---|
| EP | 0 747 021 A2 | 12/1996 |
| EP | 1 525 859 A2 | 4/2005 |
| WO | WO 98/53761 A1 | 12/1998 |
| WO | WO 02/05885 A2 | 1/2002 |
| WO | WO 2004/004597 A2 | 1/2004 |
| WO | WO 2005/034811 A1 | 4/2005 |
| WO | WO 2005/107644 A1 | 11/2005 |
| WO | WO 2007/005799 A1 | 1/2007 |
| WO | WO 2007/022395 A1 | 2/2007 |
| WO | WO 2008/042266 A2 | 4/2008 |
| WO | WO 2009/012061 A1 | 1/2009 |
| WO | WO 2010/040009 A1 | 4/2010 |
| WO | WO 2010/078352 A1 | 7/2010 |
| WO | WO 2011/094527 A1 | 8/2011 |
| WO | WO 2012/099731 A1 | 7/2012 |

(56) References Cited

FOREIGN PATENT DOCUMENTS

| WO | WO 2012/099732 A1 | 7/2012 |
|----|-------------------|--------|
| WO | WO 2012/118638 A1 | 9/2012 |

OTHER PUBLICATIONS

Written Opinion of the International Searching Authority for International Application No. PCT/US2009/069721 mailed Feb. 19, 2010.
International Search Report and Written Opinion of the International Searching Authority for International Application No. PCT/US2008/069019, dated Oct. 17, 2008, 9 pages.
International Search Report and Written Opinion of the International Searching Authority for International Application No. PCT/US2009/069721, dated Feb. 19, 2010, 9 pages.
International Search Report and Written Opinion of the International Searching Authority for International Application No. PCT/US2011/022903, dated Mar. 24, 2011, 9 pages.
International Search Report and Written Opinion of the International Searching Authority for International Application No. PCT/US2012/020597, dated May 21, 2012, 11 pages.
International Search Report for International Application No. PCT/US2012/020598, dated May 10, 2012, 4 pages.
International Search Report and Written Opinion of the International Searching Authority for International Application No. PCT/US2012/025895, dated Jun. 6, 2012, 12 pages.
Albee, F., "Bone Surgery with Machine Tools," Scientific American, Apr. 1936, pp. 178-181.

* cited by examiner

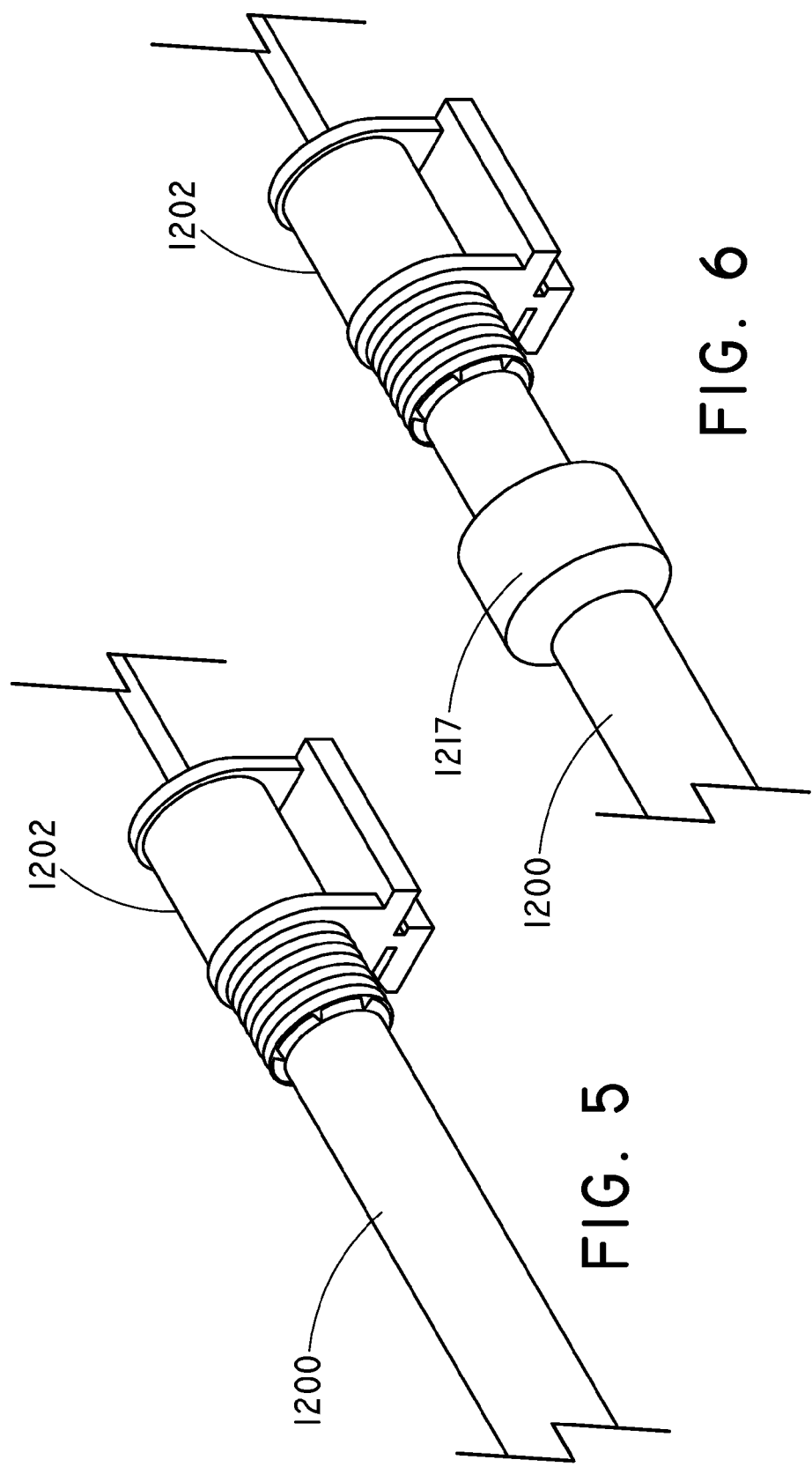

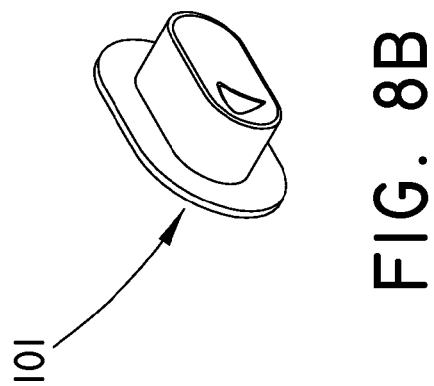
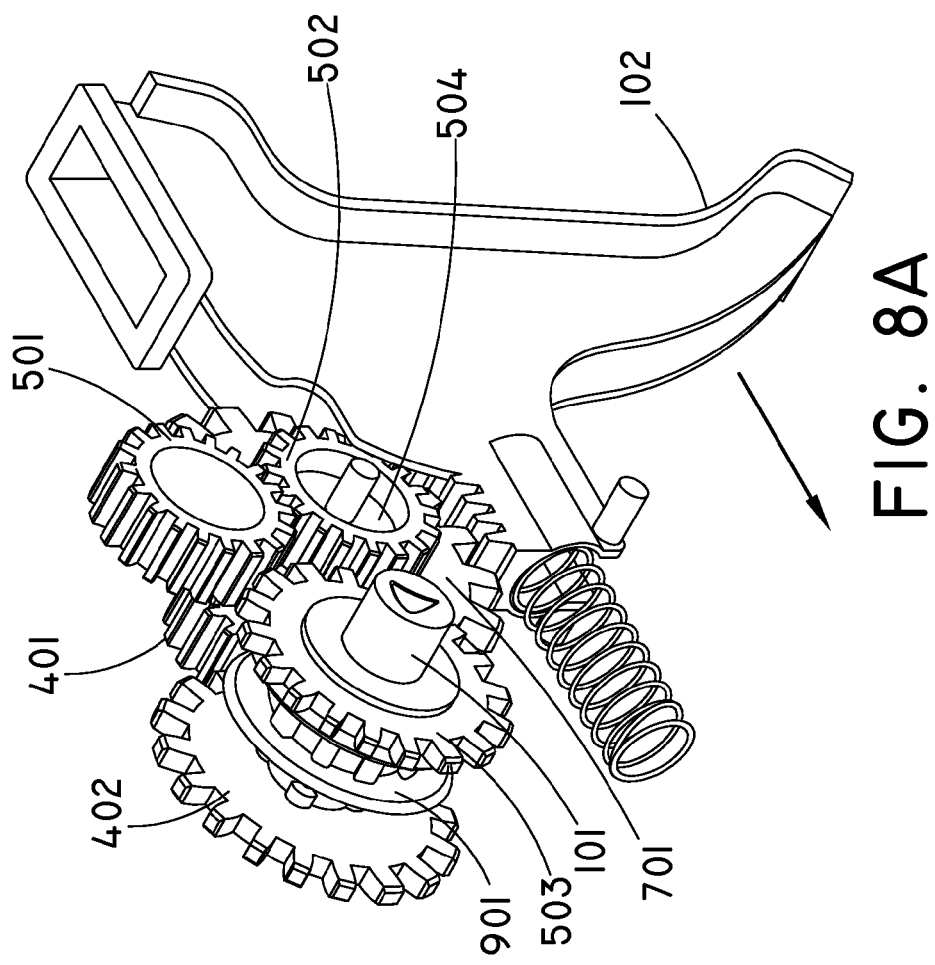

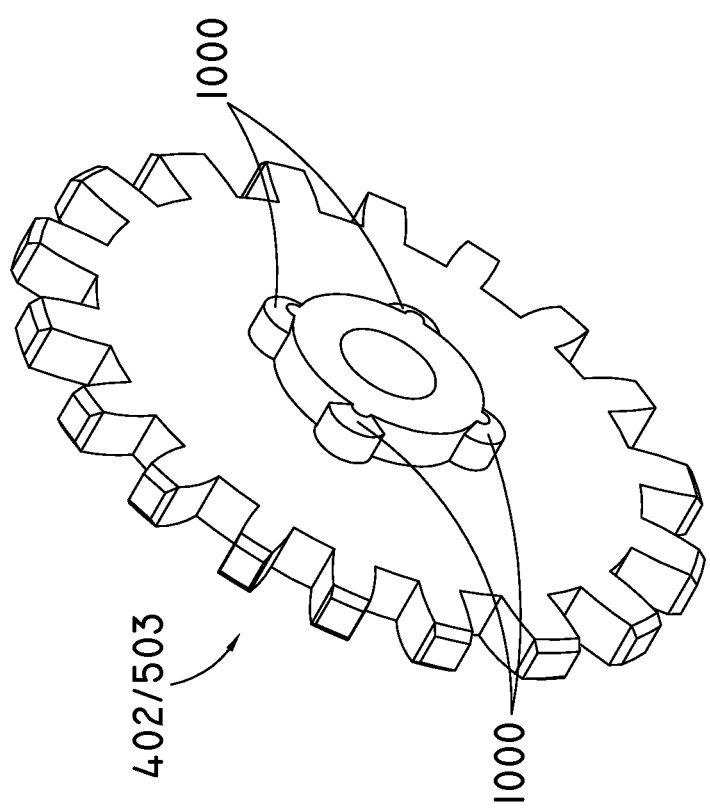

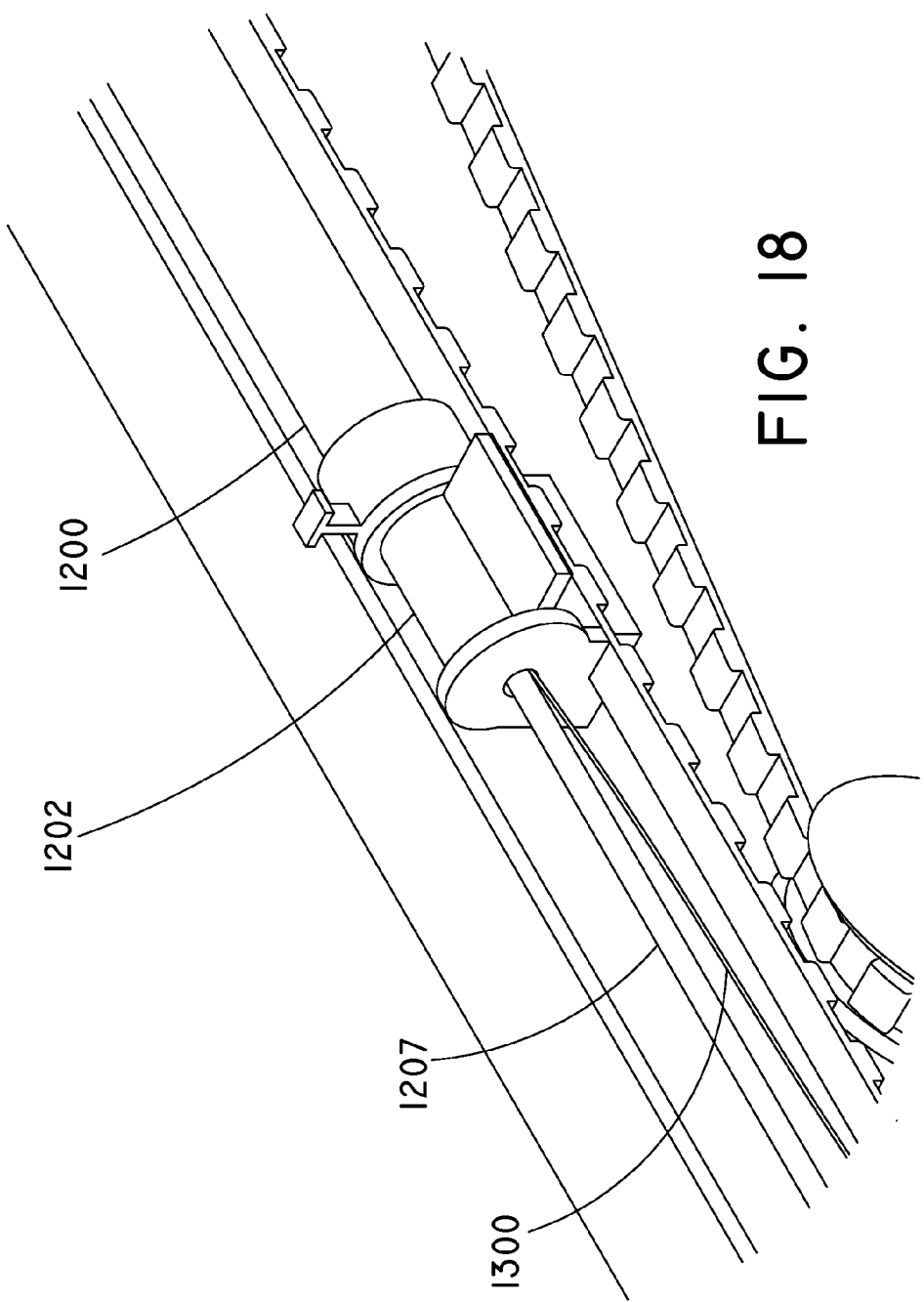

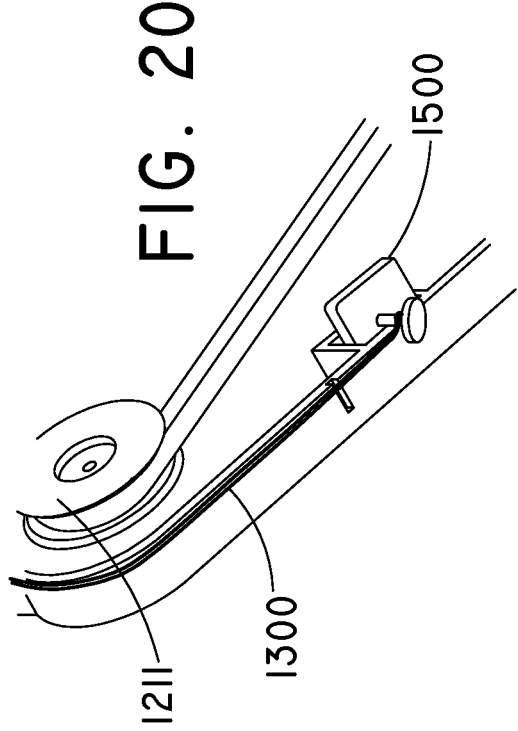
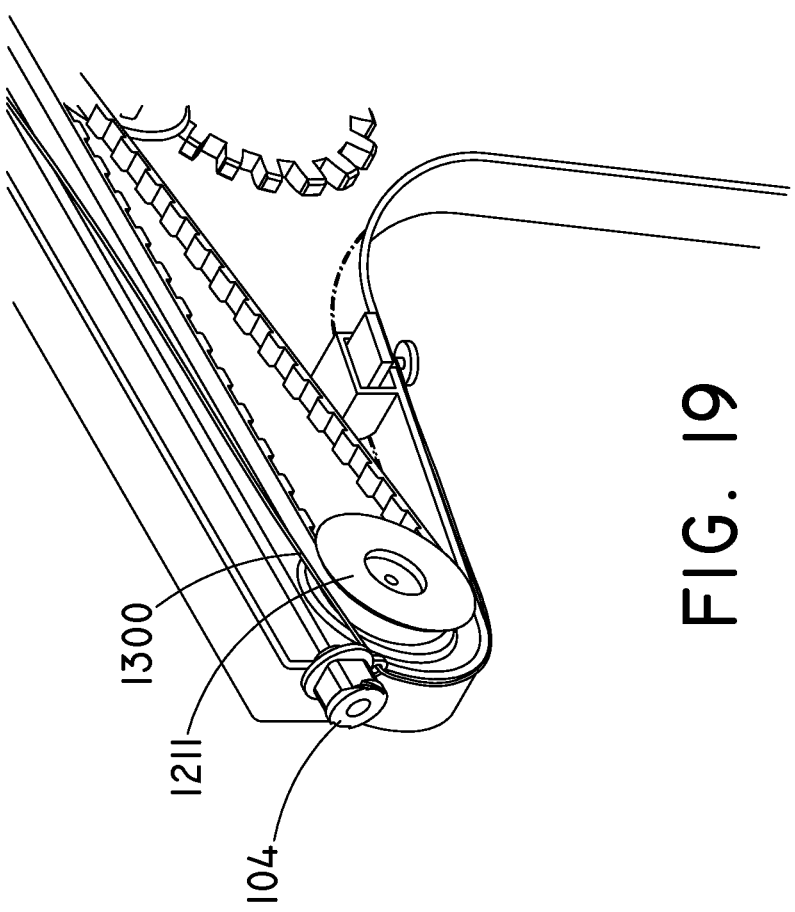

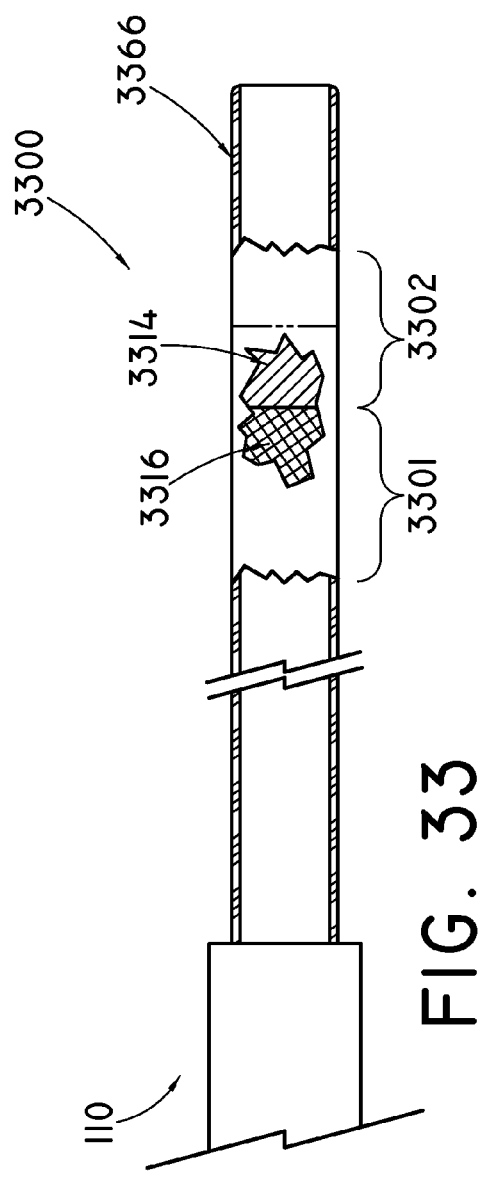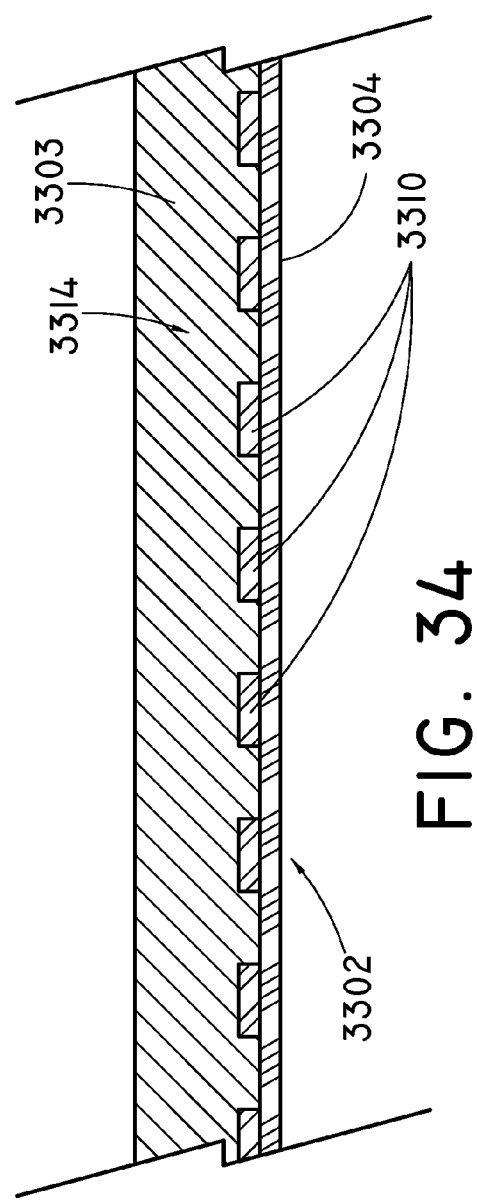

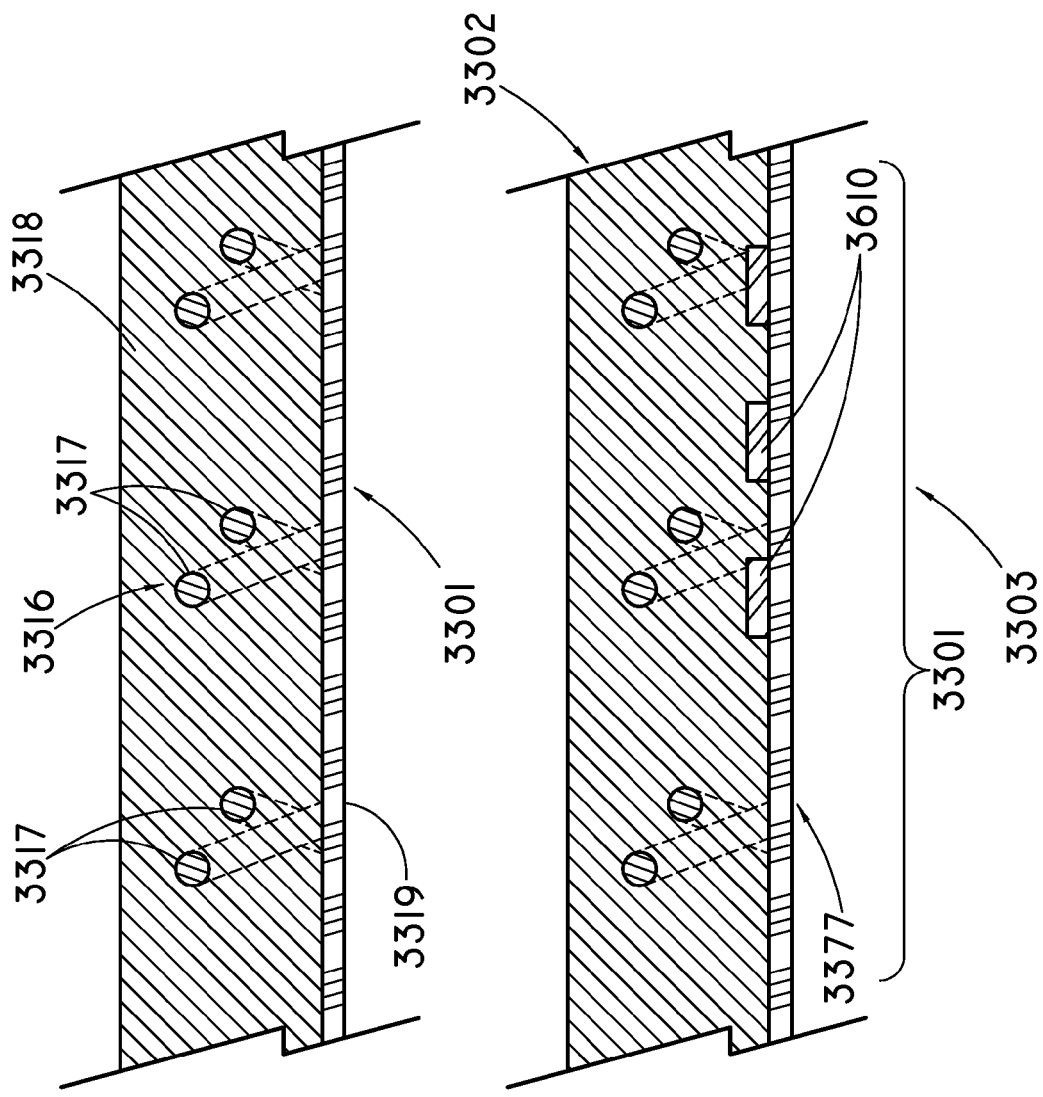

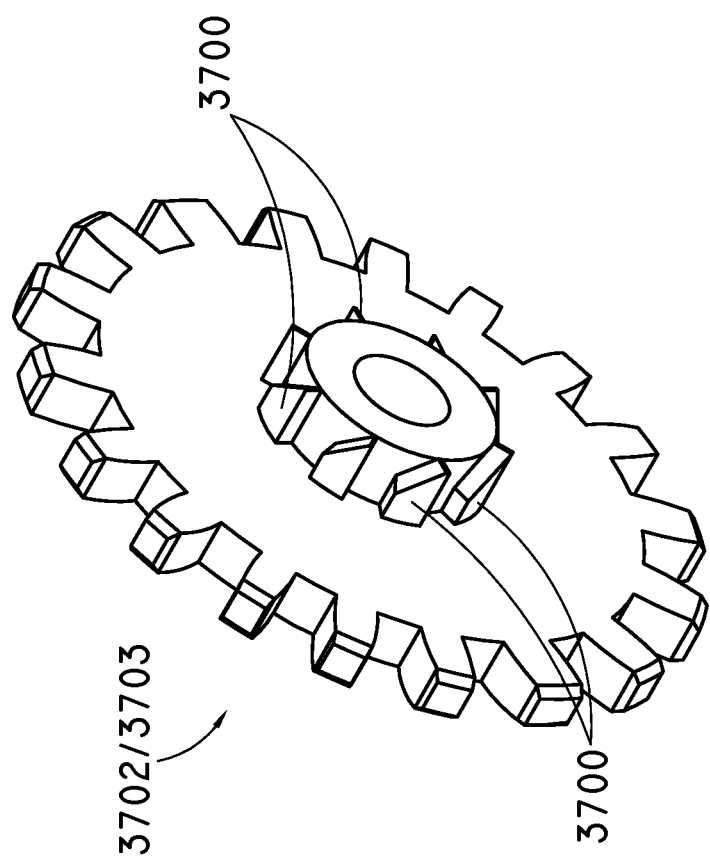

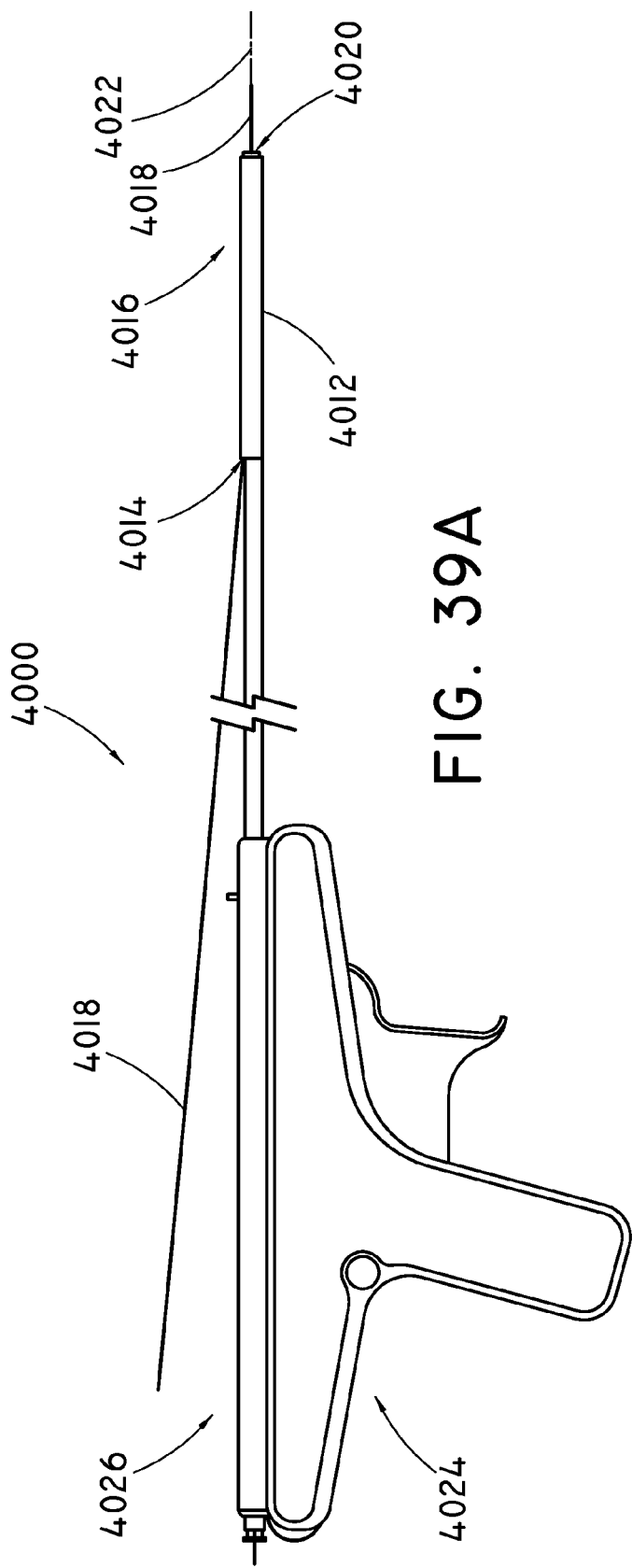
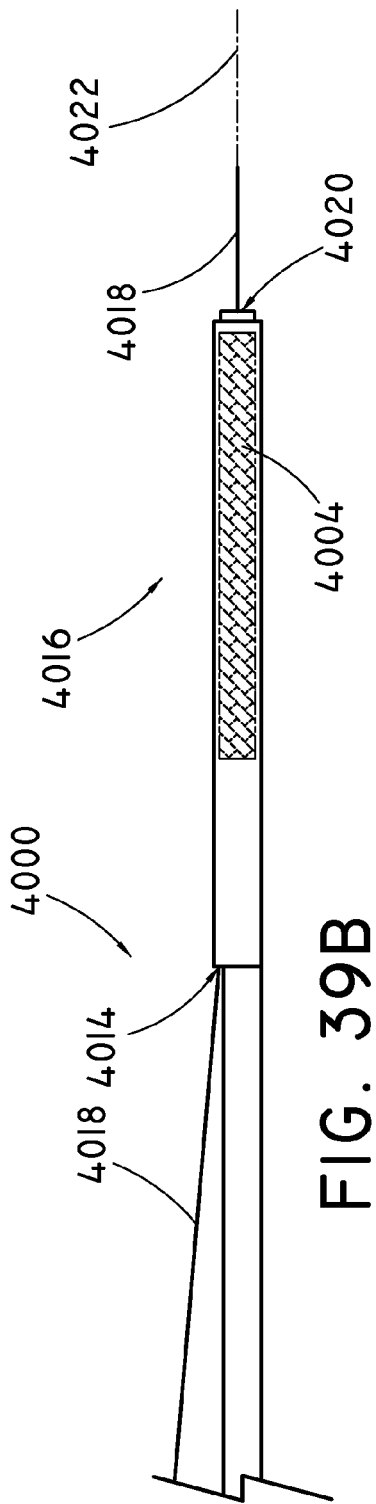

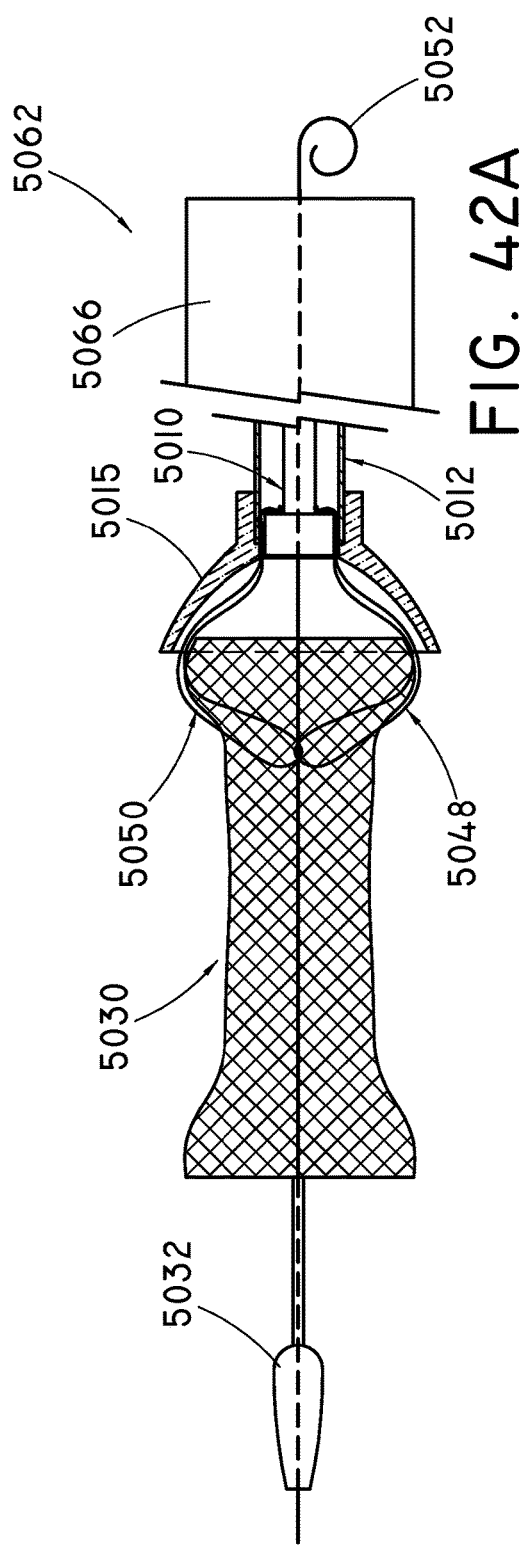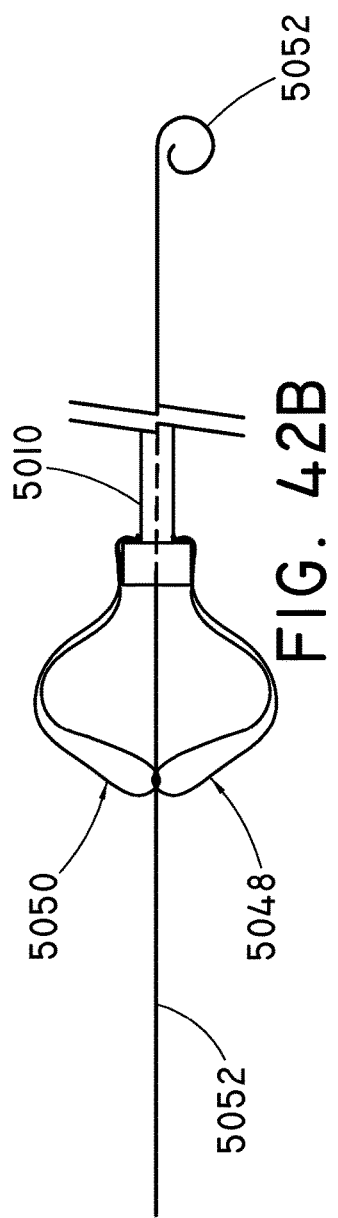
FIG. 42A
FIG. 42B

DELIVERY DEVICE

CROSS-REFERENCE TO RELATED APPLICATIONS

This application claims the benefit of U.S. Provisional Application No. 61/141,455, filed Dec. 30, 2008, which is incorporated herein by reference in its entirety.

TECHNICAL FIELD

This invention relates to a medical device and, in particular to a delivery device for a self-expanding prosthesis and a method of delivering and deploying the prosthesis into a body lumen.

BACKGROUND

A self-expanding prosthesis is typically introduced into the body using a delivery device that comprises a push-pull mechanism. The delivery device comprises an outer catheter coaxially disposed and slidable over an inner catheter. The prosthesis is disposed at the distal end of the device in between the inner catheter and the outer catheter. The inner and the outer catheter move coaxially with respect to each other. The prosthesis may be deployed by proximally pulling back the outer catheter relative to the inner catheter until the prosthesis is exposed.

There are numerous drawbacks to the above push-pull delivery device. For example, utilizing a conventional push-pull delivery device may cause the physician to inadvertently use excessive force and pull back the outer catheter too far, thereby prematurely deploying the prosthesis in an incorrect position within a body lumen. At this step in the procedure, repositioning of the prosthesis becomes difficult, if not impossible, because the prosthesis has already radially self-expanded into the body lumen. Additionally, retraction of the outer sheath is not achieved with controlled movement because the physician is manually retracting the outer catheter. Manual retraction of the outer catheter may lead to inadvertent jerking back of the outer catheter. Furthermore, two hands are typically needed to deploy the prosthesis with a push-pull mechanism. One hand may be required to hold the inner catheter while the other hand pulls the outer catheter and slides it back over the inner catheter. The use of two hands prevents the physician from performing another task during the procedure.

Accordingly, in view of the drawbacks of current technology, there is a desire for a delivery system that can increase the control, accuracy and ease of placement during deployment of a prosthesis. Although the inventions described below may be useful for increasing the control, accuracy and ease of placement during deployment of the prosthesis, the claimed inventions may also solve other problems.

SUMMARY

Accordingly, a delivery device is provided comprising an outer catheter that is capable of retracting in a proximal direction and resheathing over the prosthesis in a distal direction.

The invention may include any of the following aspects in various combinations and may also include any other aspect described below in the written description or in the attached drawings. In a first aspect, a delivery device for delivering an intraluminal device is provided. The device comprises a gear and pulley mechanism comprising a first gear set and a second gear set. A drive pulley is also provided that is adapted to be alternatively mechanically coupled to the first gear set and the second gear set. A reinforced outer sheath is disposed over an inner elongate member. The reinforced outer sheath comprises a proximal section reinforced with a braid, a distal section reinforced with a coil and an overlapping section extending between the proximal section and the distal section. The overlapping section comprises a proximal portion of the coil affixed to a distal portion of the braid. The reinforced outer sheath is in mechanical communication with the drive pulley so as to retract in a proximal direction and resheath in a distal direction.

In a second aspect, an apparatus for delivering an intraluminal device is provided. The device comprises a gear and pulley mechanism comprising a first gear set and a second gear set. A drive pulley is adapted to be alternatively mechanically coupled to the first gear set and the second gear set. An outer sheath is disposed over an inner elongate member. The sheath is in mechanical communication with the drive pulley so as to retract in a proximal direction and resheath in a distal direction. A stabilizing element comprises an anchorage assembly, the anchorage assembly comprising a retaining loop assembly and a lockwire. Engagement of a distal portion of the lockwire with the retaining loop assembly anchors the intraluminal device to the inner elongate member during movement of the outer sheath relative to the inner elongate member.

In a third aspect, a delivery device for delivering an intraluminal device is provided. The device comprises a gear and pulley mechanism comprising a first gear set and a second gear set, and a drive pulley adapted to be alternatively mechanically coupled to the first gear set and the second gear set. A reinforced outer sheath is disposed over an inner elongate member. The reinforced outer sheath comprises a proximal reinforced section and a distal reinforced section. The reinforced outer sheath is in mechanical communication with the drive pulley so as to retract in a proximal direction and resheath in a distal direction. A static tube is disposed within the reinforced outer sheath at a distal end of a handle of the delivery device. The static tube comprises a predetermined number of slits along a longitudinal length of the static tube. The slits are configured to receive a proximal portion of a stabilizing element so as to create a weaving of the stabilizing element into and out of the slits.

BRIEF DESCRIPTION OF THE DRAWINGS

Embodiments will now be described by way of example with reference to the accompanying drawings, in which:

FIG. 5 shows the end of the outer catheter flared and pushed up against a shuttle;

FIG. 6 shows a shuttle cap being screwed to the shuttle to secure the outer catheter to the shuttle;

FIG. 8A shows the trigger, drive gears and pulley gears;

FIG. 8B shows an enlarged view of the directional switch;

FIG. 9 shows protrusions on one of the faces of the pulley gear that is configured to slot into corresponding slotted ribs located on the center drive pulley;

FIGS. 18-21 show an alternative stabilizing element for fixating the stent during the resheathing of the outer catheter;

FIG. 33 shows a cross-sectional view of a reinforced outer sheath;

FIG. 34 shows a cross-sectional view of a distal section of the outer sheath, the distal section reinforced with a coil;

FIG. 35 shows a cross-sectional view of a proximal section of the reinforced outer sheath, the proximal section being reinforced with a braid;

FIG. 36 shows an overlapping section of the reinforced outer sheath in which the coil proximally extends into the proximal section of the outer sheath to overlap with the braid;

FIG. 37 shows an alternative embodiment of a pulley gear;

FIGS. 39A-40B show an embodiment of a delivery system having a short wire configuration;

FIGS. 42A-42B show an alternative embodiment of the delivery system shown in FIGS. 41A-41C.

DETAILED DESCRIPTION OF THE PREFERRED EMBODIMENTS

Figure 1:
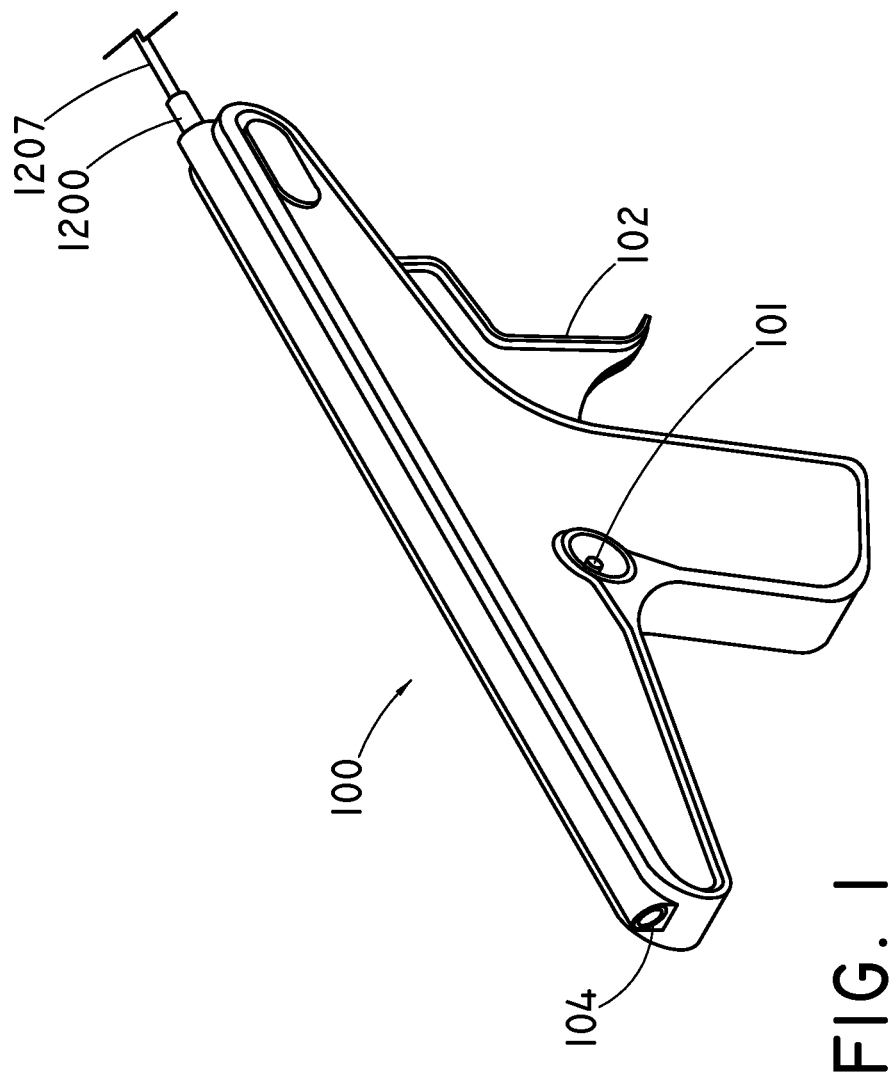
FIG. 1 is a perspective view of a delivery device.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

Throughout the specification, the terms "distal" and "distally" shall denote a position, direction, or orientation that is generally away from the physician. Accordingly, the terms "proximal" and "proximally" shall denote a position, direction, or orientation that is generally towards the physician.

Referring now to the drawings in FIGS. 1-38, a delivery device for deploying a self-expanding prosthesis is shown. As will be discussed, the delivery device has the ability to resheath and reposition the prosthesis, thereby substantially increasing the control and accuracy of the deployment process as compared with conventional delivery devices.

Figure 4:
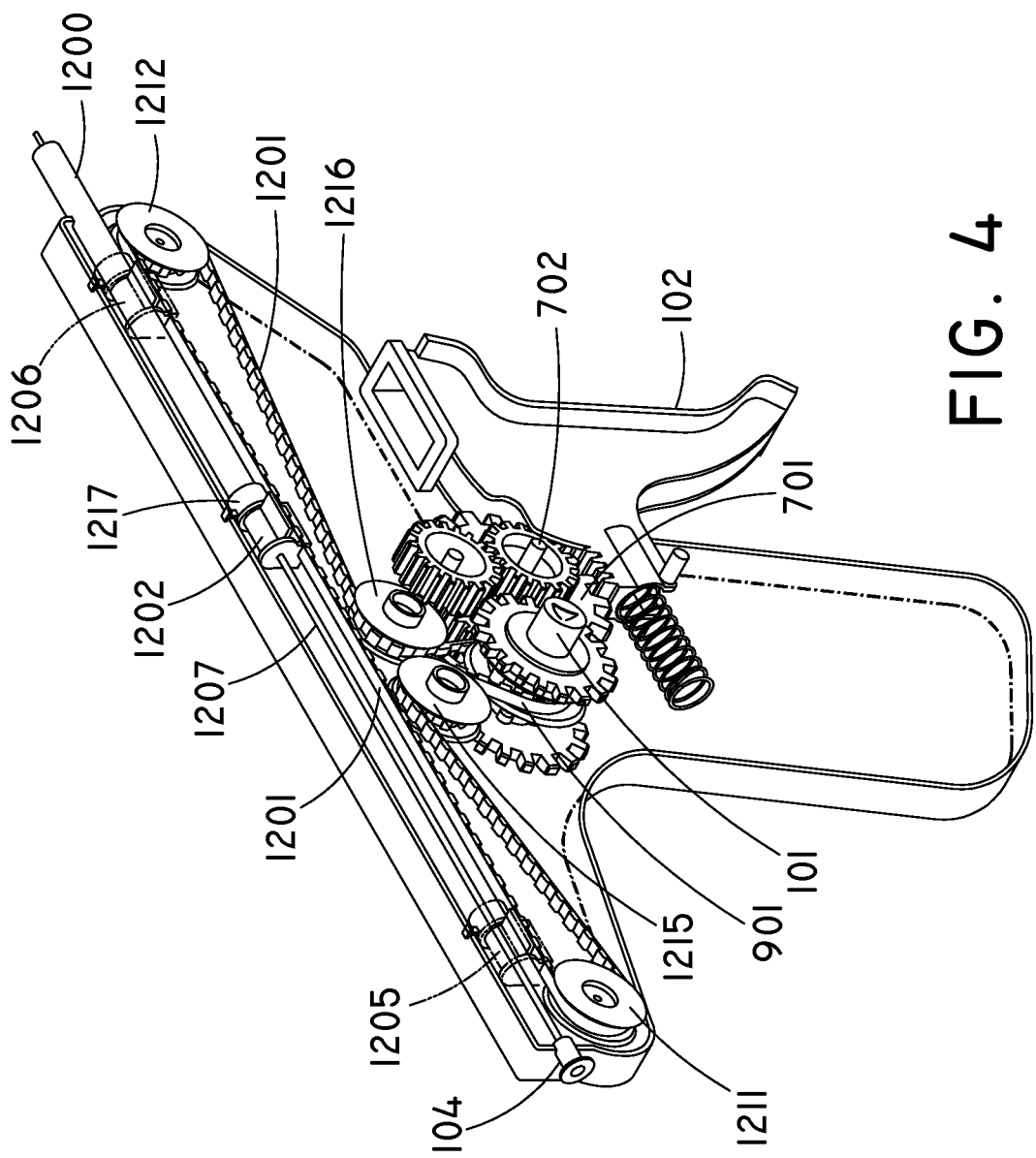
FIG. 4 is a perspective view of the delivery device showing the outer catheter connected to a belt.

FIG. 1 shows an exemplary delivery device 100. The inner catheter 1207 and outer catheter 1200 are shown exiting the distal end of the device 100. The inner catheter 1207 remains fixated to the delivery device 100 at the rear hub 104. The outer catheter 1200 may be affixed to a movable belt 1201 (FIG. 4). Actuation of a spring-loaded trigger 102 pulls the outer catheter 1200 in the proximal direction relative to the inner catheter 1207 to expose the self-expanding prosthesis. A directional switch 101 may be engaged to reverse the direction of the outer catheter 1200 prior to actuating the trigger 102. An internal gear-pulley mechanism enables the bidirectional movement of the outer catheter 1200.

Figure 2:
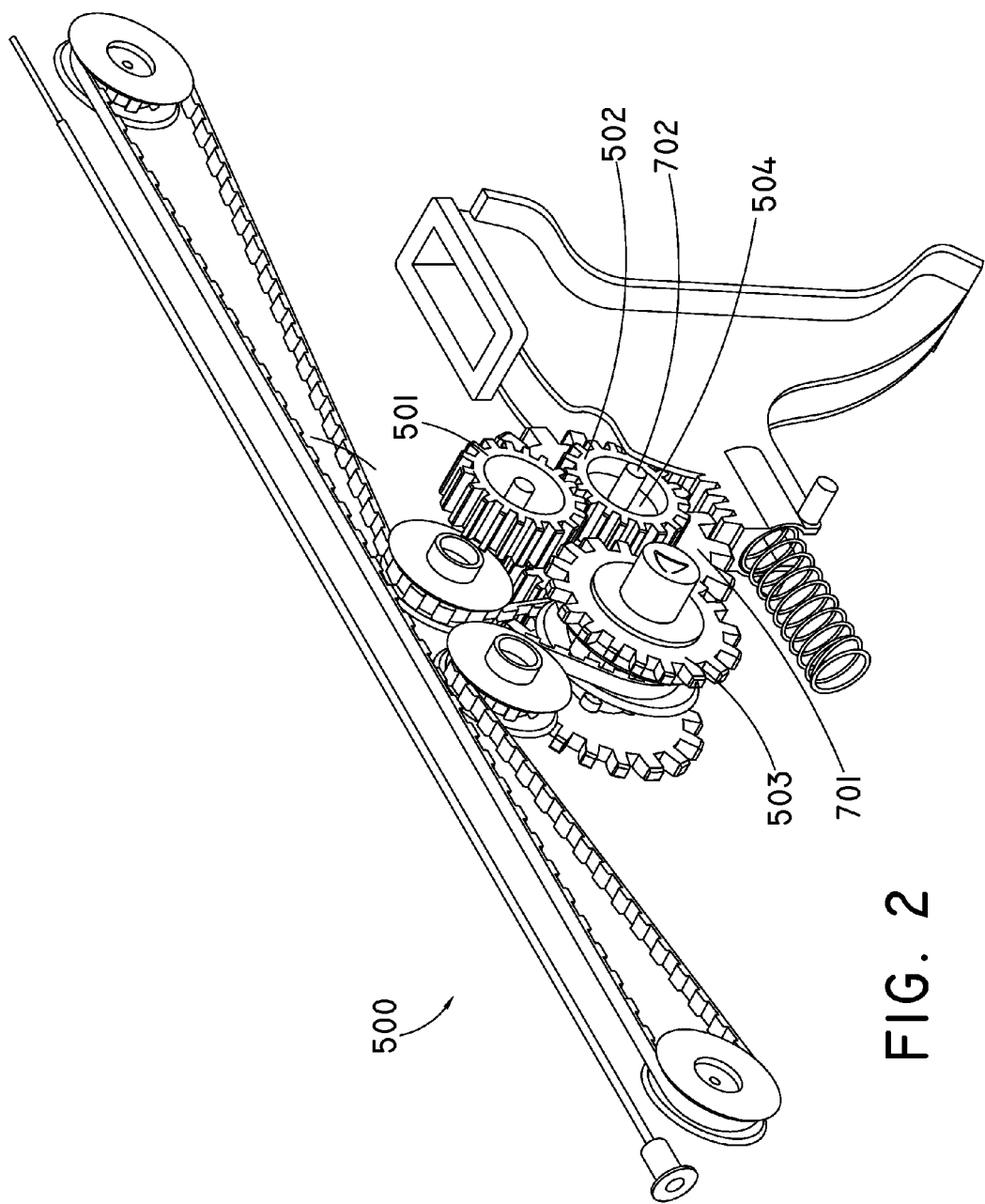
FIG. 2 is a perspective view of a first gear set of the delivery device.

A first gear set resheaths the outer catheter 1200 (i.e., moves the outer catheter 1200 in a distal direction relative to the inner catheter 1207) and a second gear set retracts the outer catheter 1200 (i.e., moves the outer catheter 1200 in a proximal direction relative to the inner catheter 1207). FIG. 2 shows the first gear set 500. The first gear set 500 comprises a first drive gear 502, a first idle gear 501, and a first pulley gear 503. The first drive gear 502 is mechanically engaged with the first idle gear 501. The first idle gear 501 is mechanically engaged with the first pulley gear 503. The first drive gear 502 has a one-directional roller clutch bearing 504. Specifically, the roller clutch bearing 504 is press fit within the inner surface of the first drive gear 502 and allows for rotation of the first drive gear 502 in only one direction, which will be explained in greater detail below.

Figure 3:
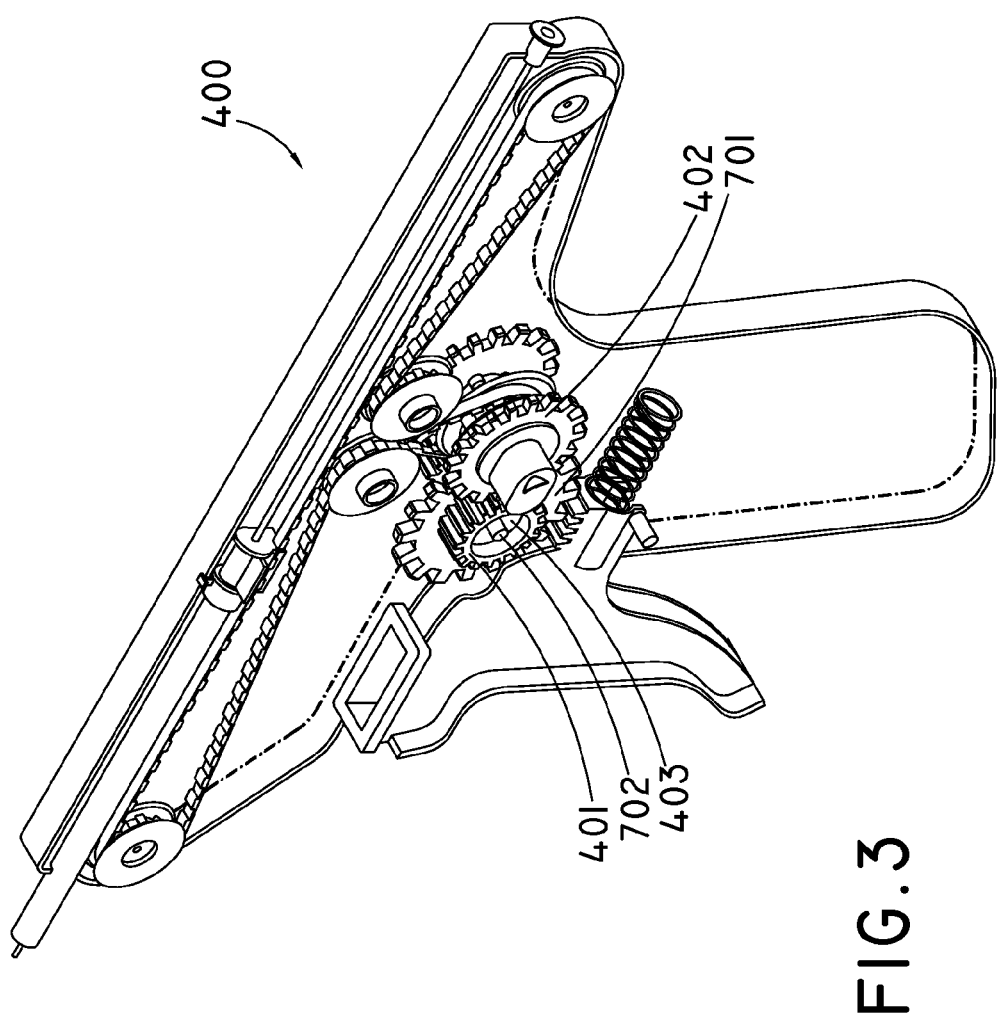
FIG. 3 is a perspective view of a second gear set of the delivery device.

FIG. 3 shows the second gear set 400. The second gear set 400 comprises a second drive gear 401 and a second pulley gear 402. The second drive gear 401 is mechanically coupled to the second pulley gear 402. Similar to the first drive gear 502, the second drive gear 401 also comprises a roller clutch bearing 403 that allows for rotation of the gear 401 in only one direction, which will be explained in greater detail below.

Figure 12:
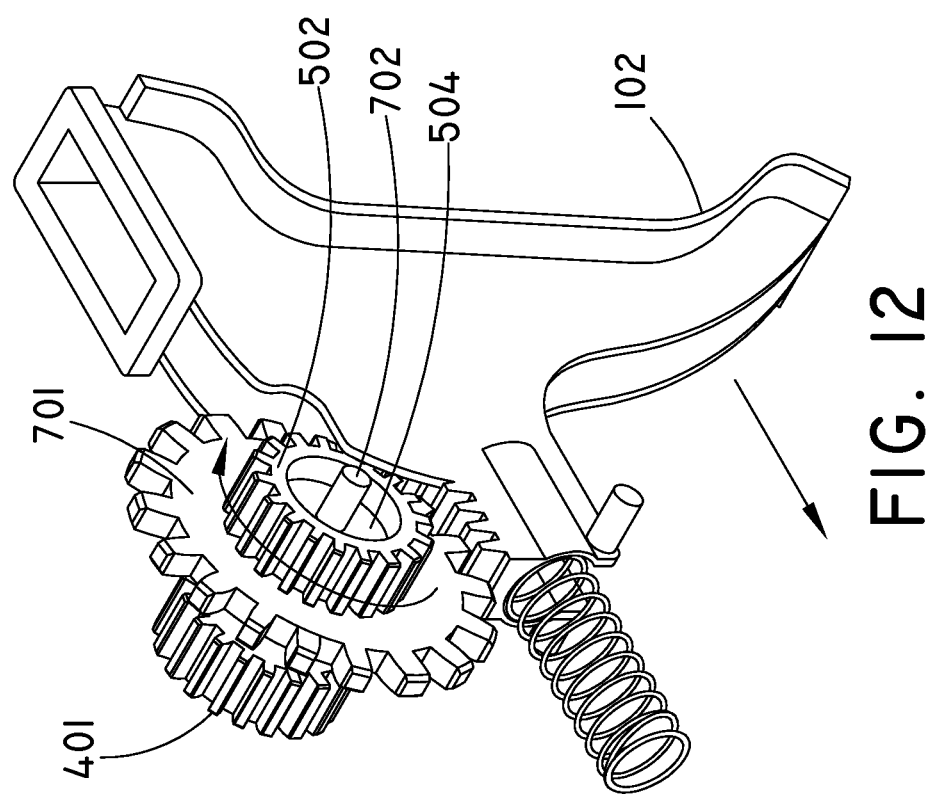
FIG. 12 shows the trigger and the drive gears.

A drive shaft 702 extends through the clutch bearing 403 of the second drive gear 401 (FIG. 3) and through the clutch bearing 504 of the first drive gear 502 (FIG. 2). A main drive gear 701 is rotationally fixed to the drive shaft 702, as clearly seen in FIG. 27. The main drive gear 701 is also engaged with a trigger 102 (FIG. 12). The trigger 102 includes a rack 709 having complimentary teeth 704 (FIG. 11) that engage with the main drive gear 701.

Proximal and distal movement of the outer catheter 1200 may be allowed by the outer catheter 1200 being connected to a belt 1201, as shown in FIG. 4. The outer catheter 1200 is affixed to a shuttle 1202 and the shuttle 1202 is connected to a belt 1201. FIGS. 5 and 6 show how the outer catheter 1200 is affixed to the shuttle 1202. FIG. 5 shows that the end of the outer catheter 1200 may be flared and pushed up against the shuttle 1202. After abutting the flared end of the outer catheter 1200 against the shuttle 1202, FIG. 6 shows that a shuttle cap 1217 may be coupled to the shuttle 1202. Specifically, the cap 1217 may be screwed onto the threads of the shuttle 1202 to secure the outer catheter 1200 to the shuttle 1202. The inner catheter 1207 may be secured to the rear hub 104 in a similar manner. Other types of attachments of the outer catheter 1200 to the belt 1201 are contemplated.

Figure 7:
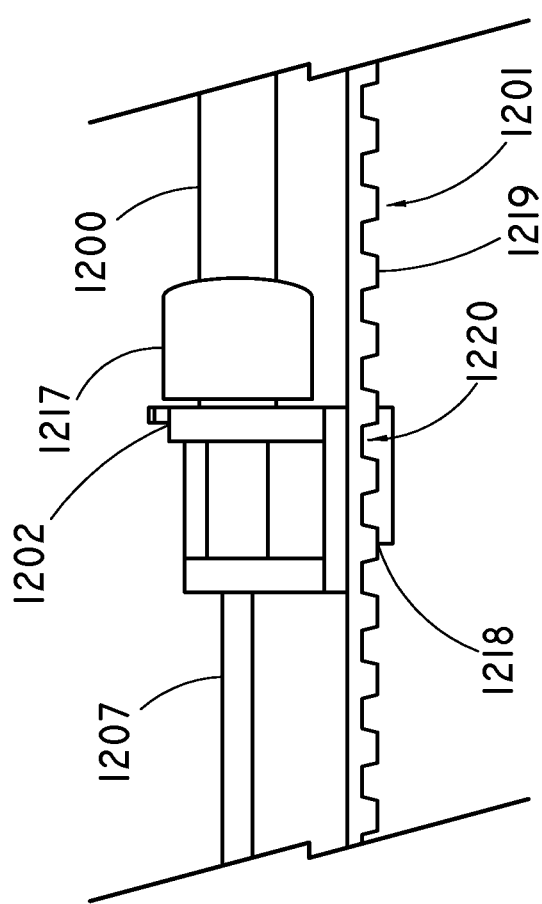
FIG. 7 shows the attachment of the belt to the shuttle and outer catheter.

The attachment of the belt 1201 to the shuttle 1202 and outer catheter 1200 may be seen in FIG. 7. FIG. 7 shows that the shuttle 1202 contains an opening 1218 through which belt 1201 may extend. The shuttle 1202 contains corresponding grooves 1220 that engage with protrusions 1219 of the belt 1201 to establish a secure belt-shuttle connection. Movement of the belt 1201 causes the shuttle 1202 and outer catheter 1200 attached thereto to laterally move along the belt 1201 in the proximal direction or distal direction.

Referring to FIG. 4, activation of the first gear set 500 or the second gear set 400 rotates a center drive pulley 901 and the belt 1201 to cause the shuttle 1202 with the outer catheter 1200 attached thereto to move with the belt 1201. FIG. 4 illustrates possible positions that the outer catheter 1200 may have. The most reverse position of the shuttle 1202 and belt 1201 is indicated at position 1205. The most forward position of the shuttle 1202 and belt 1201 is indicated at position 1206. For purposes of clarity, the shuttle cap 1217 is not shown at positions 1205 and 1206. As the outer catheter 1200 moves along the belt 1201, the inner catheter 1207 remains stationary because the inner catheter 1207 is fixated at the proximal end of the device 100 at the rear hub 104.

Referring to FIG. 8A, desired belt 1201 movement is achieved by engaging a center drive pulley 901 with the first pulley gear 503 or the second pulley gear 402. The first pulley gear 503 and the second pulley gear 402 are slidable along a shaft to engage and disengage with the drive pulley 901. The engagement and disengagement may occur by the ribs or protrusions 1000 of the pulley gears 503, 402 slidably engaging with the ribbed slots 902 of the center drive pulley 901. Directional switch 101 allows the first pulley gear 503 or the second pulley gear 402 to engage with the center drive pulley 901. FIG. 8B illustrates an exemplary directional switch 101. Referring to FIG. 8A, the first pulley gear 503, second pulley gear 402, and directional switch 101 extend along a shaft (not shown). Pushing the directional switch 101 against the first pulley gear 503 causes the first pulley gear 503 to engage with the center drive pulley 901 and the second pulley gear 402 to disengage with the center drive pulley 901 along the shaft. At any given time, the center drive pulley 901 may be engaged to either the first pulley gear 503 or the second pulley gear 402.

Figure 10:
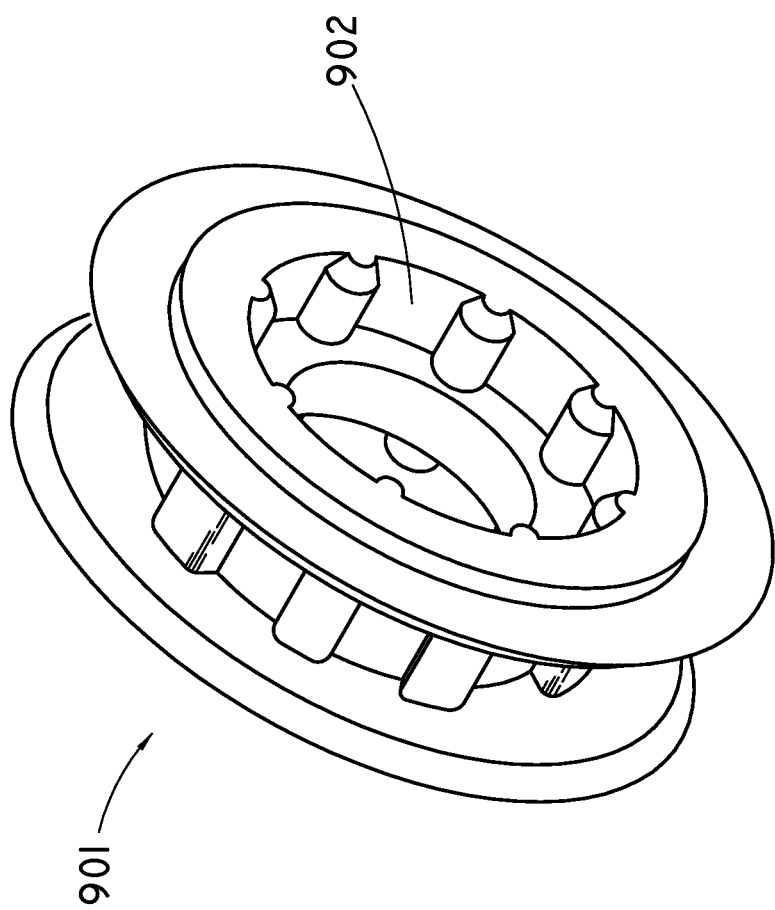
FIG. 10 shows ribbed slots on the center drive pulley that are configured to receive the pulley gears.
Figure 11:
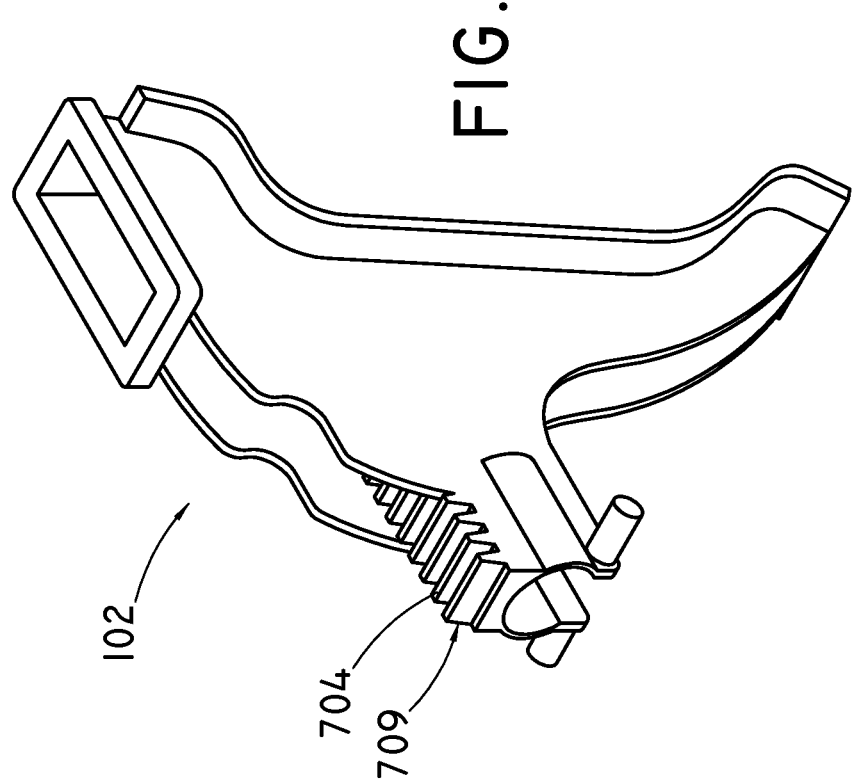
FIG. 11 shows the rack of the trigger of the delivery device.

The engagement of the first or second pulley gears 503, 402 with the center drive pulley 901 can be understood by referring to FIGS. 9 and 10. The first and second pulley gears 503 and 402 may appear as shown in FIG. 9. FIG. 10 shows that the center drive pulley 901 contains ribbed slots 902 that correspond to protrusions 1000 (FIG. 9) of the first and second pulley gears 503, 402. The multiple side protrusions 1000 of the first and second pulley gears 503, 402 (FIG. 9) slide into the ribbed slots 902 located on the side of the center drive pulley 901 (FIG. 10) to lockably engage with each other. The engagement may be such that when the locked first pulley gear 503 or locked second pulley gear 402 rotates, the center drive pulley 901 will rotate in the same direction, thereby transferring the motion of the pulley gears 503, 402 to the drive pulley 901 and belt 1201.

Figure 38:
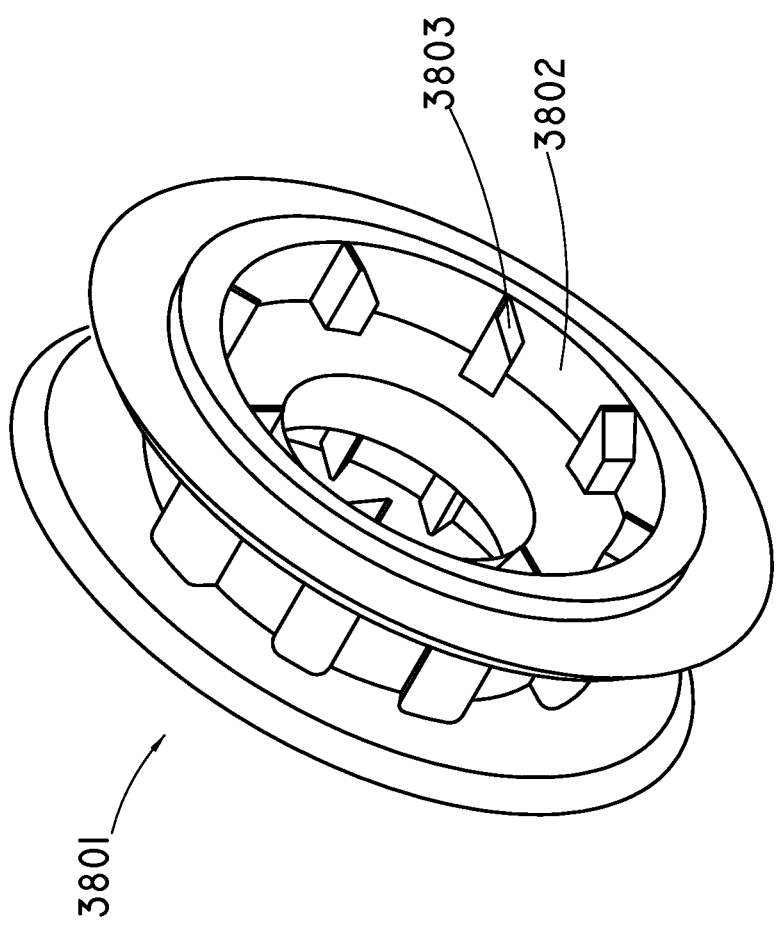
FIG. 38 shows an alternative embodiment of a center drive pulley designed to engage with the pulley gear of FIG. 37.

The first and second pulley gears 503 and 402 may comprise a greater number of ribbed slots 902 compared to that shown in FIG. 9 to facilitate engagement of the pulley gears 503 and 402 with the center drive pulley 901. Alternatively, or in addition, the shape of the ribbed slots 902 of the center drive pulley 901 may be modified to enhance its engagement with the gears 503 and 402. FIG. 37 shows an example of an alternative embodiment of a first and second pulley gear 3702 and 3703 having angled slots 3700. The shape and greater number of slots 3700 may provide improved engagement of the gears 3702 and 3703 with the center drive pulley 3801 shown in FIG. 38. FIG. 38 shows that center drive pulley 3801 contains multiple slots 3802, each of which are defined by adjacently disposed angled structures 3803. The shape of each of the slots 3802 corresponds to the shape of each of the angled slots 3700 (FIG. 37) to allow a secure fit therewithin.

The belt 1201 is shown in FIG. 4 to be wrapped around three pulleys 1211, 1212 and 901. Pulleys 1211 and 1212 may help transfer gear movement into belt movement. Center drive pulley 901 engages with one of the first gear set 500 and the second gear set 400 to cause rotational movement of the belt 1201. Although a three pulley system is shown, more than three pulleys or less than three pulleys are contemplated.

Idlers 1215 and 1216 (FIG. 4) may help to provide wrapping a sufficient amount of the belt 1201 around the center drive pulley 901 for the purpose of preventing belt 1201 slippage from the center drive pulley 901. Referring to FIG. 4, the belt 1201 wraps around idler 1215 and then proceeds down and around the center drive pulley 901. The belt 1201 then proceeds up and around the top of idler 1216. FIG. 4 shows that the idlers 1215, 1216 help the belt 1201 to wrap around more than 180° of the center drive pulley 901.

The gear mechanism for resheathing (i.e., the outer catheter 1200 moving from the proximal direction to the distal direction as indicated by the arrow in FIG. 4) will now be explained. Reference to the rotational movement of the various gears and pulleys will be made in accordance with perspective views facing the first gear set 500 (FIGS. 4, 8, 11, 12). The directional switch 101 is pushed such that the first pulley gear 503 is engaged with the center drive pulley 901 and the second pulley gear 402 is disengaged from the center drive pulley 901 (FIG. 8A). Pulling the trigger 102 in the proximal direction, as indicated by the arrow in FIG. 8A, causes the main drive gear 701 to engage with the rack 709 (FIG. 12) of the trigger 102 (FIG. 11) and rotate in a clockwise direction (the three arrows in FIG. 12 around first drive gear 502 represent clockwise rotation). Because the main drive gear 701 is directly connected to the drive shaft 702, the drive shaft 702 also rotates in a clockwise direction. As the drive shaft 702 rotates in a clockwise direction, the first drive gear 502 and the second drive gear 401 also rotate in the same direction. The first drive gear 502 is engaged to the first idle gear 501 and therefore clockwise rotation of the first drive gear 502 causes the first idle gear 501 to rotate counterclockwise (FIG. 8A). The first idle gear 501 is engaged to a first pulley gear 503. Accordingly, counterclockwise rotation of the first idle gear 501 causes the first pulley gear 503 to rotate clockwise (FIG. 8A). Because the directional switch 101 has been pushed to engage the first pulley 503 with the center drive pulley 901 (FIG. 8A), the center drive pulley 901 also rotates in the clockwise direction. With the belt 1201 winding around a center drive pulley 901, two idlers 1215 and 1216 pull in the belt 1201 around the center drive pulley 901, as shown in FIG. 4. The idlers 1215 and 1216 optimize the connection between the belt 1201 and the center drive pulley 901 to minimize slippage of the belt 1201 around the center drive pulley 901. Clockwise rotation of the center drive pulley 901 also causes the belt 1201 to rotate clockwise (FIG. 4). The clockwise rotation of the belt 1201 causes the shuttle 1202 and outer catheter 1200 attached thereto to resheath or move proximally to distally (FIG. 4).

When the trigger 102 has been deactivated so that the trigger 102 moves distally and returns to its original position, the drive shaft 702 and main drive gear 701 rotate counterclockwise and return to their original position. The drive shaft 702 is permitted to rotate counterclockwise within the one-directional roller clutch bearings 403, 504. However, roller clutch bearings 403, 504 prevent the left and right drive gears 401, 502 from rotating counterclockwise upon the trigger 102 being deactivated. Thus, the first and second drive gears 502 and 401 will remain in the position from which they have rotated clockwise after activation of the trigger 102. The effect of having the first drive gear and the second drive gears 502 and 401 rotate clockwise but not counterclockwise is that the outer catheter 1200 may continue to be incrementally moved in a proximal (i.e., retractable direction) or distal direction (i.e., resheathing direction). Accordingly, this unidirectional movement of the first and second drive gears 502 and 401 is converted into movement of the belt 1201.

The gear mechanism for retracting the outer catheter 1200 (i.e., the outer catheter 1200 moving from the distal direction to the proximal direction) will now be explained. Reference to the rotational movement of the various gears and pulleys will be made in accordance with perspective views facing the second gear set 400 (FIG. 3). The directional switch 101 is pushed such that the second pulley gear 402 is engaged with the center drive pulley 901 and the first pulley gear 503 is disengaged from the center drive pulley 901. Referring to FIG. 3, pulling the trigger 102 in the proximal direction as indicated by the arrow causes the main drive gear 701 to engage with the rack 709 (FIG. 11) of the trigger 102 and rotate in a counterclockwise direction. Because the main drive gear 701 is directly connected to the drive shaft 702, the drive shaft 702 also rotates in a counterclockwise direction. As the drive shaft 702 rotates in a counterclockwise direction, the first drive gear 502 and the second drive gear 401 rotate in the same direction. Because the second drive gear 401 is engaged to the second pulley gear 402, counterclockwise rotation of the second drive gear 402 causes the second pulley gear 402 to rotate clockwise (FIG. 3). The engagement of the second pulley gear 402 with the center drive pulley 901 causes the center drive pulley 901 to also rotate in a clockwise direction (FIG. 3).

Figure 13:
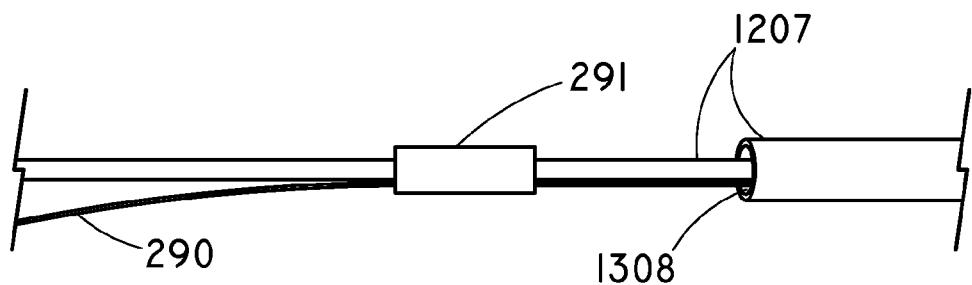
FIGS. 13-16 illustrate the steps of affixing one end of a retaining wire through the crowns of the stent.

Referring to FIG. 3, the rotation of the second pulley gear 402 with the center drive pulley 901, which was seen as clockwise from the perspective in FIG. 2, becomes viewed as counterclockwise from the perspective in FIG. 3. The counterclockwise rotation of the center drive pulley 901 also causes the belt 1201 to rotate counterclockwise. The counterclockwise rotation of the belt 1201 causes the shuttle 1202 and outer catheter 1200 attached thereto to retract or move distally to proximally (FIG. 12), thereby exposing the self-expanding prosthesis. As FIG. 13 shows, a step 1308 is formed where the smaller and larger diameter portions of the inner catheter 1207 meet, which prevents the prosthesis from being pulled back proximally with the outer sheath 1200.

The unidirectional movement of the first and second drive gears 502 and 401 is converted into proximal movement of the belt 1201 and outer catheter 1200 attached thereto. Specifically, when the trigger 102 has been deactivated so that the trigger 102 moves distally and returns to its original position, the drive shaft 702 and main drive gear 701 rotate clockwise with respect to FIG. 3 and return to their original position. The drive shaft 702 is permitted to rotate clockwise within the one-directional roller clutch bearings 403, 504. However, roller clutch bearings 403, 504 prevent the left and right drive gears 401, 502 from rotating upon the trigger 102 being deactivated. The effect of having the first drive gear and the second drive gears 502 and 401 rotate counterclockwise but not clockwise (as shown in FIG. 3) is that the outer catheter 1200 may continue to be incrementally moved in a proximal direction (i.e., retractable direction).

In order to prevent the self-expanding prostheses from moving as the outer catheter 1200 moves during resheathing, a stabilizing element is affixed to the prosthesis. The stabilizing element maintains the prosthesis in a substantially stationary position during the resheathing of the outer catheter 1200 over the prosthesis, as will now be explained.

Figure 14:
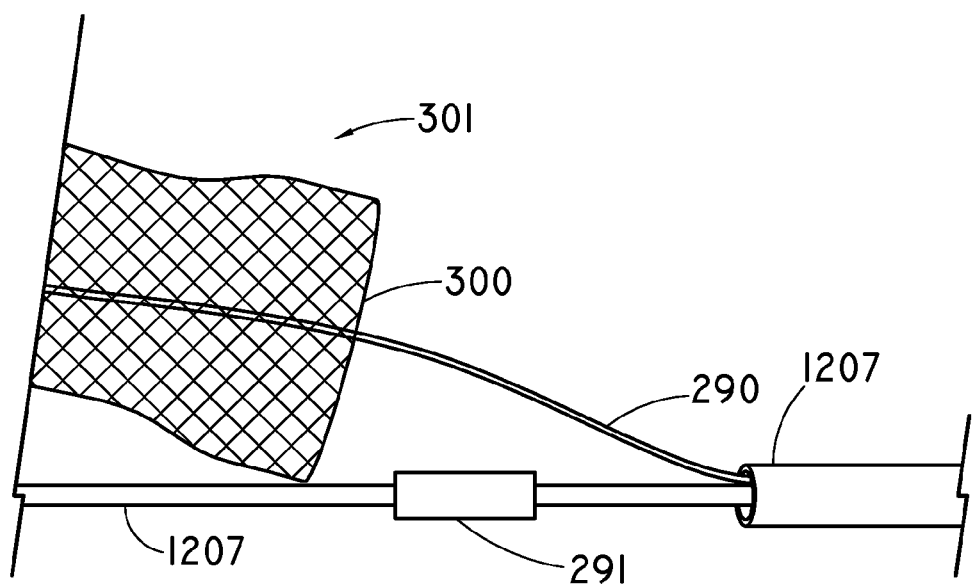
Figure 15:
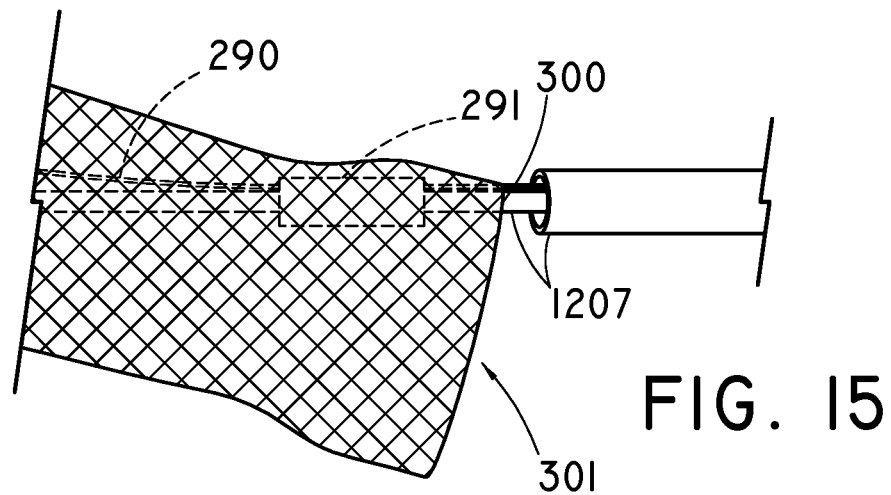
Figure 16:
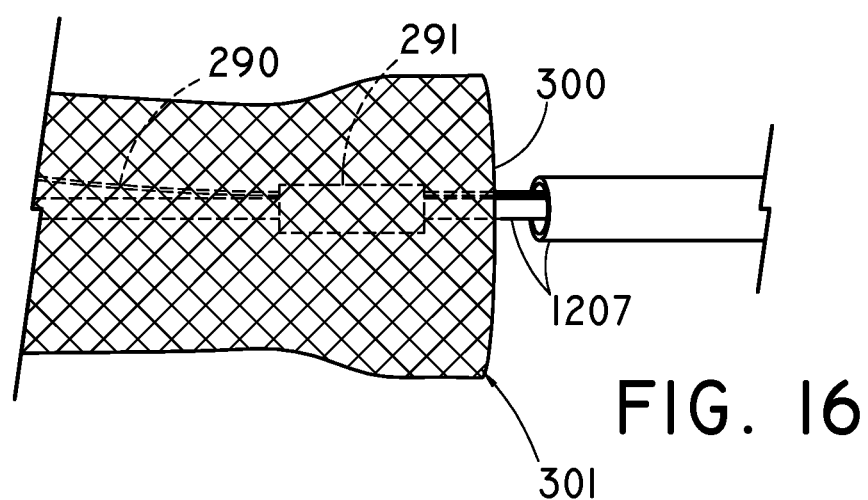
Figure 17:
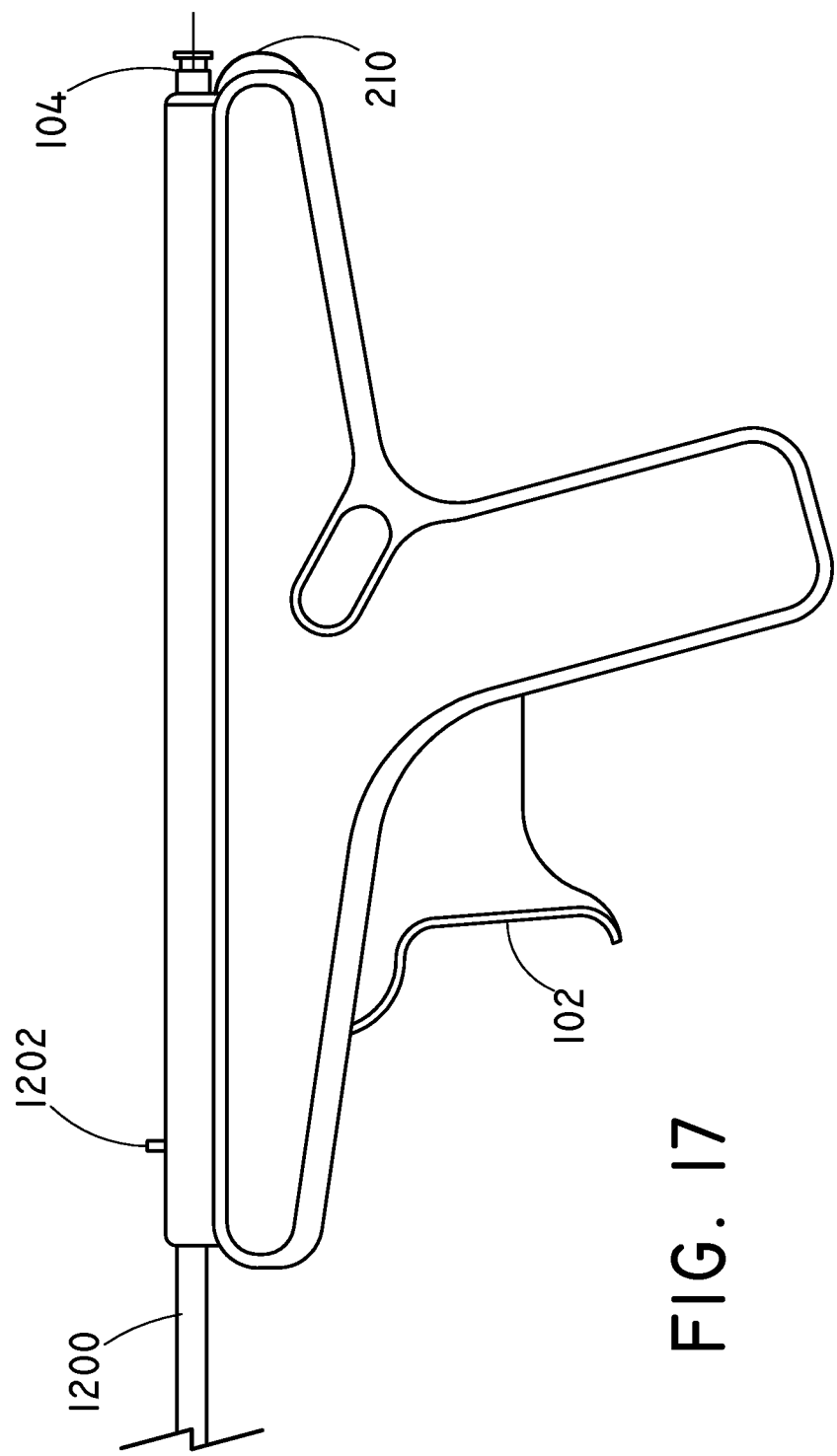
FIG. 17 is a perspective view of a handle portion of the delivery device.
Figure 27:
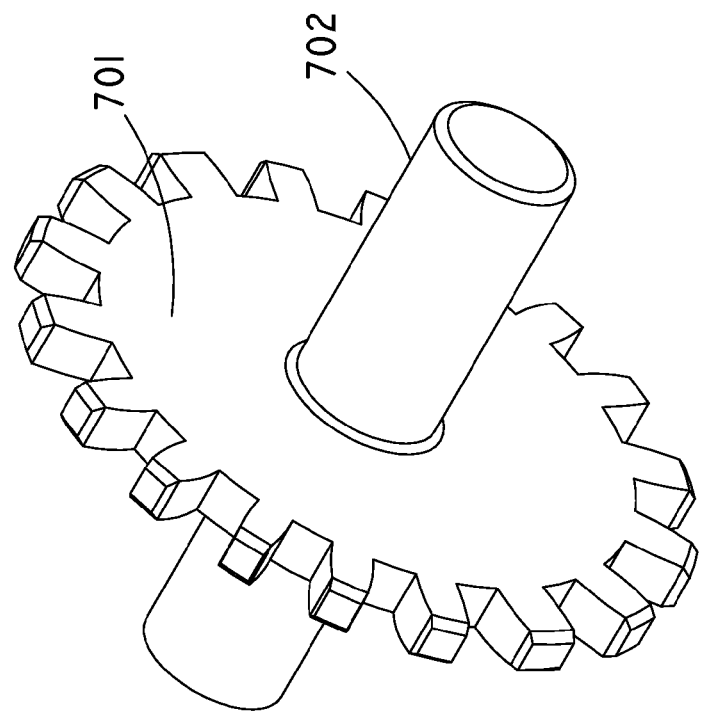
FIG. 27 shows a main drive gear rotationally fixed to the drive shaft.

Various types of stabilizing elements are contemplated. FIGS. 13-16 show the steps involved in loading and anchoring a preferred type of stabilizing element to a self-expanding stent. FIGS. 13-16 show that the stabilizing element may be a retaining wire 290. The proximal end of the retaining wire 290 is anchored to a ring 210 at the rear hub 104 of the inner catheter 1207, as shown in FIG. 17. The wire 290 extends along the longitudinal length of the device 100. The proximal portion of the wire 290 is disposed between the inner catheter 1207 and the outer catheter 1200. As the wire 290 extends distally from the rear hub 104, the wire 290 enters into a slit of the inner catheter 1207 and longitudinally travels therein in the distal direction until it emerges from the larger diameter portion of the inner catheter 1207 as shown in FIG. 14, which shows a stent 301 being loaded into the device 100. FIG. 14 shows that as the wire 290 emerges from the inner catheter 1207, it passes through one of the crowns 300 of a self-expanding stent 301. FIG. 14 shows that the wire 290 extends distally from the end portion of the stent 301 and may terminate at the body portion of the stent 301. At this juncture, the distal end of the wire 290 is maneuvered to extend through a lumen of a piece of bilumen tubing 291 (FIG. 15), which is affixed (e.g., glue) to the inner catheter 1207. The smaller diameter portion of the inner catheter 1207 is configured to extend through the proximal end of the stent 301 as shown in FIG. 15. The distal end of the wire 290 exits the lumen of the bilumen tubing 291. The distal end of the wire 290 is a free end that terminates within the lumen of the stent 301, as shown in FIGS. 15 and 16. The free end preferably does not interact with the stent 301.

The retaining wire 290 in this configuration (FIGS. 15 and 16) anchors the stent 301 in place such that the stent 301 will not move distally as the outer catheter 1200 is being resheathed over the stent 301. Specifically, referring to FIGS. 15 and 16, the stent 301 is locked into position at its proximal end by the crown 300 which the retaining wire 290 extends through. Referring to FIG. 16, the stent 301 cannot substantially move proximally because the stent 301 is locked by the wire 290 and the larger diameter portion of the inner catheter 1207. The stent 301 cannot substantially move distally because it is locked between the wire 290 and bilumen tubing 291. The stent 301 cannot substantially move up (i.e., coming out of the plane of the page) or down (i.e., going into the plane of the page) because the wire 290 passes through the crown 300. The stent 301 may not become free until the retaining wire 290 is removed from the crown 301. Removal of the retaining wire 290 may be achieved by pulling the ring 210 at the rear hub 104 of the inner catheter 1207, as shown in FIG. 17.

The bilumen tubing 291 may be positioned anywhere along the stent 301. In the example shown in FIGS. 13-16, the bilumen tubing 291 is positioned toward the proximal end of the stent 301 for the purpose of maximizing resheathing capabilities of the outer catheter 1200. In other words, the more the bilumen tubing 291 is positioned toward the distal end of the stent 301, the greater the tendency may be for the stent 301 to move with the outer catheter 1200 during resheathing. In the example shown in FIG. 15, the bilumen tubing 291 is affixed to the smaller inner catheter 1207 and positioned about 2 mm to about 5 mm from the proximal end of the stent 301. Accordingly, the amount of lateral movement of the stent 301 during resheathing of the outer catheter 1200 may be substantially eliminated.

Figure 21:
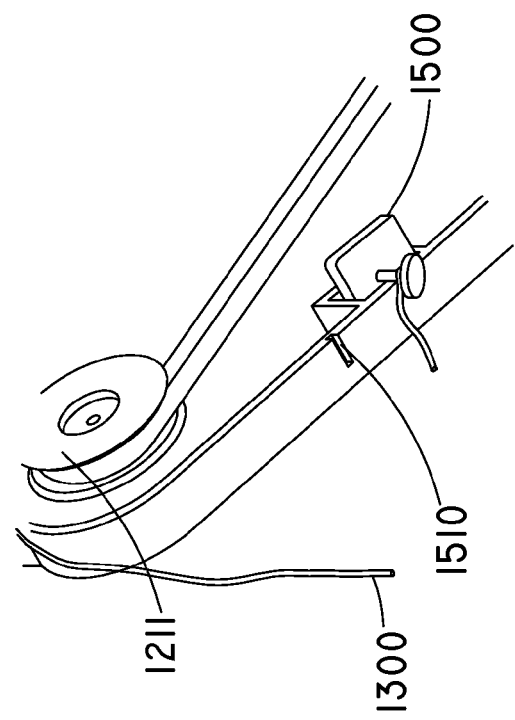

In an alternative embodiment, the stabilizing element is a suture loop 1300 may be used as shown in FIGS. 18-21. The suture loop 1300 may be looped through one or more crowns of the stent and is positioned in between the outer catheter 1200 and the inner catheter 1207. It may exit the shuttle 1202 as shown in FIG. 18. The suture loop 1300 continues to extend inside the device 100 between the inner catheter 1207 and the outer catheter 1200, as shown in FIG. 18. The suture loop 1300 exits the rear hub 104 as shown in FIG. 19. After exiting the rear hub 104, the suture loop 1300 follows a path where it is connected to the bottom of the device 100 at a post 1500 (FIG. 20). A groove 1510 (FIG. 21) located at the bottom of the device 100 may be used to cut the suture loop 1300. After the suture loop 1300 is cut, as shown in FIG. 21, the remainder of the suture loop 1300 can be pulled through the device 100 by pulling on one end of the suture 1300. Because the suture 1300 is held in place at the one or more crowns 300 of the stent and at the post 1500 of the handle (FIG. 20), the stent 301 may substantially be held in place during resheathing of the outer catheter 1200.

Figure 28:
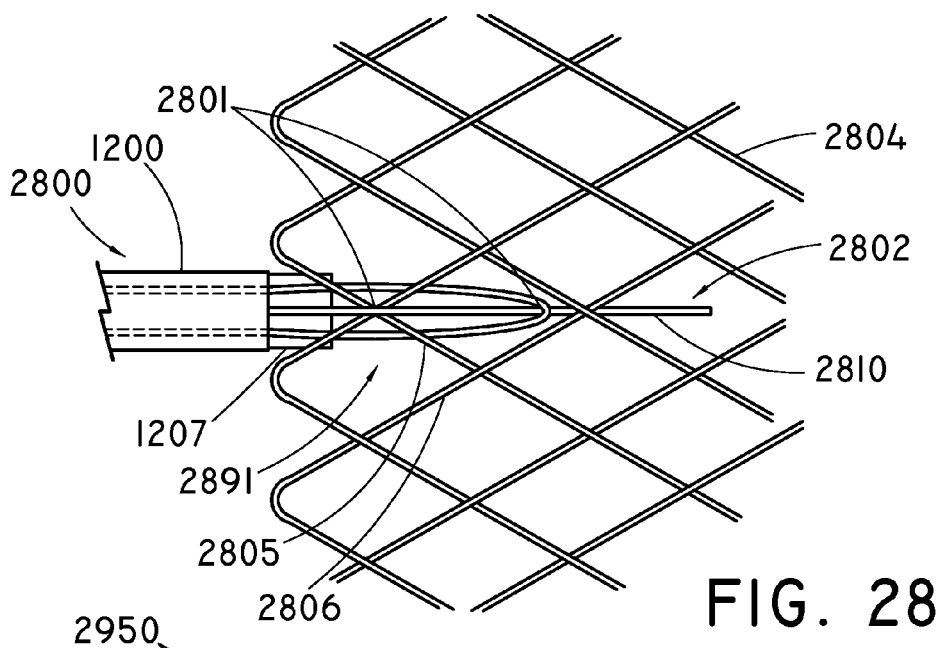
FIGS. 28-31 show an embodiments for fixating a self-expandable stent during resheathing of the outer catheter and deployment of the stent.

FIGS. 28-32 show an alternative embodiment of a stabilizing element used to fixate the stent 2804 to the inner catheter 1207 during resheathing (i.e., distal movement of the outer sheath 1200 relative to the inner catheter 1207) or deployment of the stent 2804 (i.e., proximal movement of the outer sheath 1200 relative to the inner catheter 1207). The stabilizing element comprises an anchorage assembly 2800 as shown in FIGS. 28 and 29A. FIG. 28 shows that the anchorage assembly 2800 includes a retaining loop assembly 2891 and a lockwire 2802. Engagement of the lockwire 2802 with the retaining loop assembly 2891 fixates the stent 2804 during resheathing of the outer sheath 1200 or during deployment of the stent 2804. The components of the retaining loop assembly 2891 are clearly seen in FIG. 29A. FIG. 29A shows that the retaining loop assembly 2891 includes a retaining loop wire 2930, a first pair of cannulas 2902 and 2904, and a second cannula 2903. FIG. 28 shows that the stent 2804 is anchored to the inner catheter 1207 by engagement of a lockwire 2802 through the retaining loop wire 2930, and the struts 2805 and 2806 of the stent 2804.

Figure 24:
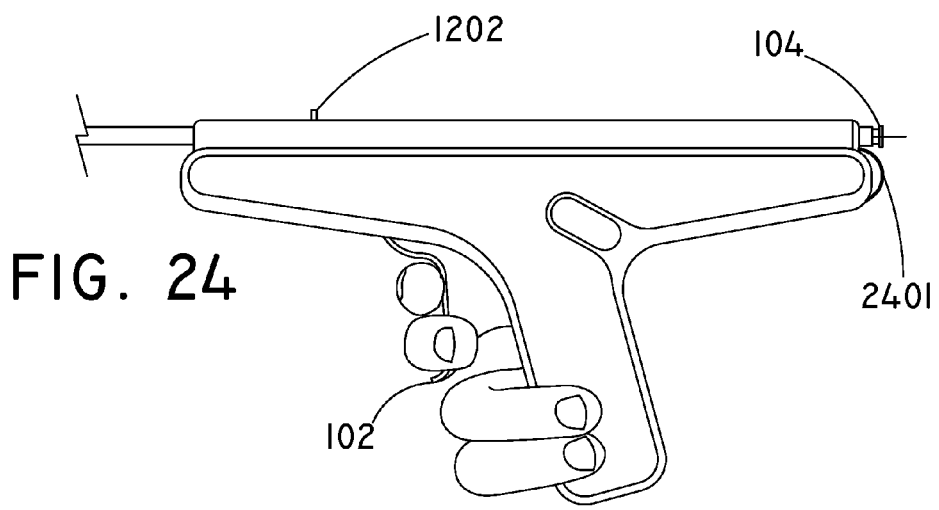
Figure 30:
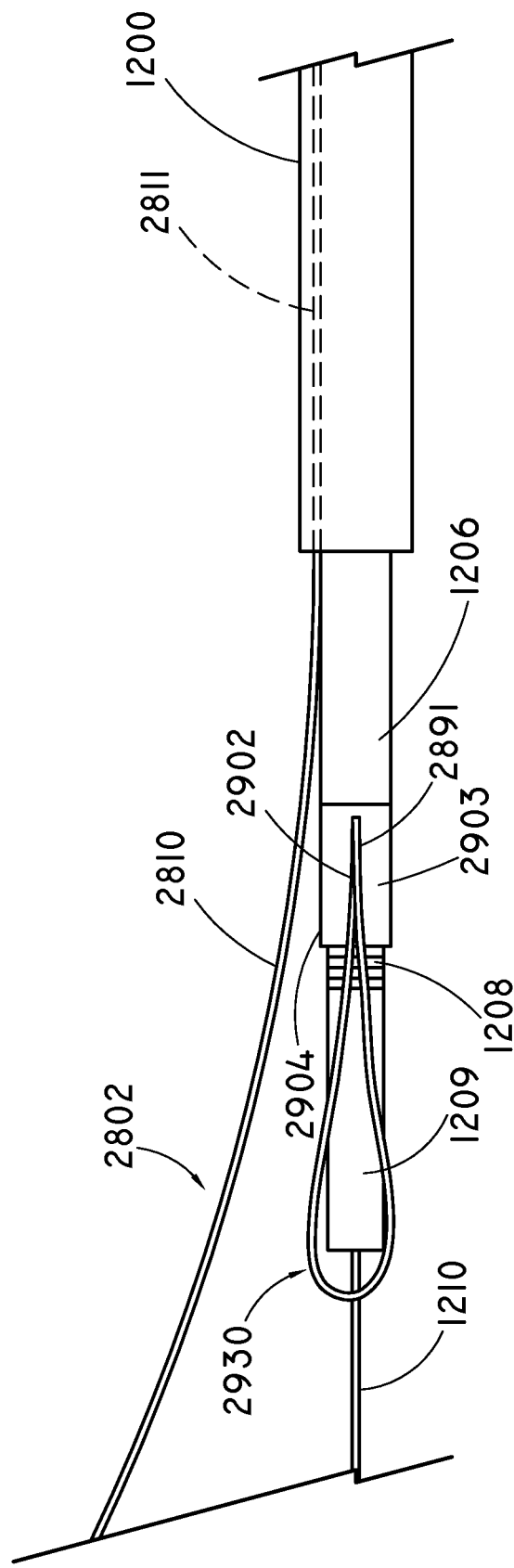

The lockwire 2802 comprises a distal portion 2810 (FIGS. 28 and 30) and a proximal portion 2811 (FIG. 30). FIG. 30 shows that the proximal portion 2811 of the lockwire 2802 extends proximally between the inner catheter 1207 and the outer sheath 1200 and terminates as a pigtail 2401 at the rear hub 104 of the handle of the device 100 (FIG. 24). FIGS. 28 and 30 show that the distal portion 2810 of lockwire 2802 distally extends out from between the outer sheath 1200 and the inner catheter 1207 towards the stent 2804. FIG. 28 shows that as the distal portion 2810 emerges from inner catheter 1207, the distal portion 2810 extends along an outside portion of stent 2804 in a distal direction and passes over the first strut 2805 of the stent 2804. After passing over the first strut 2805, the distal portion 2810 distally travels from the outside portion of the stent 2804 to the inside of the stent 2804, the distal portion 2810 of lockwire 2802 now being disposed within the luminal space of the stent 2804. With the distal portion 2810 now disposed within the luminal space of stent 2804, the distal portion 2810 of lockwire 2802 extends in the distal direction past second strut 2806 and through the retaining loop wire 2930 from the outside to the inside and past the apex 2931 (FIG. 29A) of retaining loop wire 2930. The distal portion 2810 of lockwire 2802 continues to travel a predetermined distance within luminal space of stent 2804 and eventually terminates as a distal free end (not shown) within the luminal space of stent 2804. The distal portion 2810 of the lockwire 2802 releasably locks the stent 2804 to the inner catheter 1207.

Referring to FIG. 28, the points at which the lockwire 2802, the retaining loop wire 2930, and the first strut 2805 of stent 2804 intersect each other defines anchorage points 2801. The stent 2804 remains substantially fixated to inner catheter 1207 at anchorage points 2801 during resheathing of outer sheath 1200 and also during deployment of the stent 2804. In other words, the stent 2804 remains locked to the inner catheter 1207 by anchorage assembly 2800 (i.e., retaining loop assembly 2891 and lockwire 2802). When the stent 2804 is anchored to the inner catheter 1207 at anchorage points 2801 as shown in FIG. 28, resheathing of the outer sheath 1200 over stent 2804 is possible. Additionally, because the distal portion 2810 of the lockwire 2802 remains in mechanical engagement with the retaining loop assembly 2891, full deployment of the stent 2804 into a body lumen (i.e., disengagement of stent 2804 from inner catheter 1207) is not yet possible.

Figure 31:
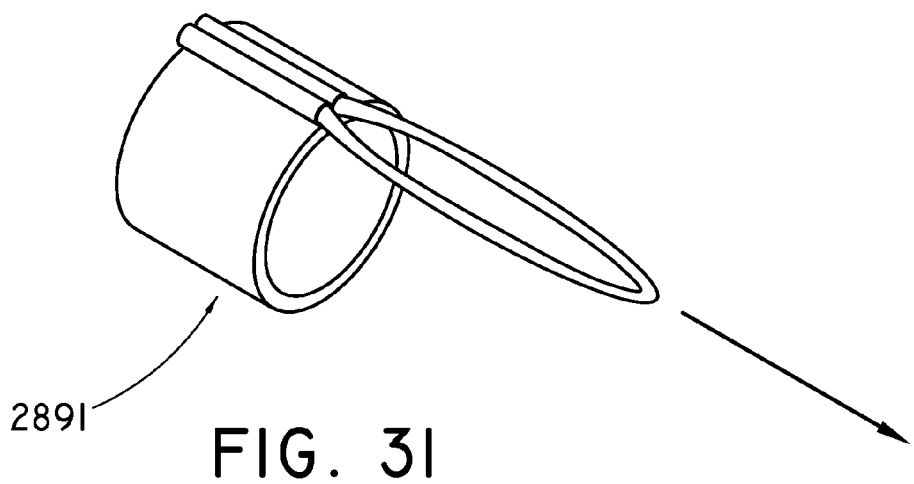

The force generated and imparted to the retaining loop assembly 2891 during resheathing can rise to about 70 Newtons of axial load during use without breakage, as shown in FIG. 31. Accordingly, it is necessary for the retaining loop assembly 2891 to maintain anchorage of the stent 2804 at such relatively high loads. Failure for the retaining loop assembly 2891 to fixate the stent 2804 at such high loads may cause the stent 2804 to slip along the inner catheter 1207 such that resheathing and/or deployment capabilities are lost. FIG. 29 shows more clearly the components of the retaining loop assembly 2891 which are designed to withstand such loads. The retaining loop wire 2930 is inserted into the first pair of cannulas 2902 and 2904. The first pair of cannulas 2902 and 2904 is shown connected to the second cannula 2903. Numerous means may be used to connect the first pair of cannulas 2902 and 2904 with second cannula 2903. For example, the first pair of cannulas 2902 and 2904 may be connected to the second cannula 2903 by an adhesive. In a preferred embodiment, the first pair of cannulas 2902 and 2904 is laser welded to the second cannula 2903. The distal portion 2932 of the retaining loop wire 2930 forms its loop shape. Specifically, the distal portion 2932 of the wire 2930 folds back upon itself to form two proximal sections 2934 and 2935, each of which is shown to extend completely through corresponding openings 2955 and 2956 of the first pair of cannulas 2902 and 2904. The proximal sections 2934 and 2935 of retaining loop wire 2930 are affixed within the inside of corresponding openings 2955 and 2956 of the first pair of cannulas 2902 and 2904 at proximal end 2950, preferably by a spot weld. Because there is no other attachment between proximal sections 2934 and 2935 other than the attachment at proximal end 2950, strain release of retaining loop wire 2930 occurs which enables substantial flexing of the loop wire 2930 without breakage. In other words, there is an absence of an abrupt transition of forces along the length of the retaining loop wire 2930 from proximal end 2950 to distal portion 2932 when the lockwire 2802 is engaged with the retaining loop wire 2930 during resheathing of the outer sheath 1200 or during deployment of the stent 2804.

Additionally, each of the cannulas 2902, 2903, 2904 and the retaining loop wire 2930 are preferably formed from materials sufficient to enable the retaining loop assembly 2891 to withstand the forces associated with pushing the outer sheath 1200 over the inner catheter 1207 during the resheathing procedure or withdrawing the outer sheath 1200 over the inner catheter 1207. In one example, each component of the retaining loop assembly 2891 (i.e., the first pair of cannulas 2902 and 2904, the second cannula 2903, and the retaining loop wire 2930) is formed from a metallic alloy, such as, for example, ASTM grade 302 or 304 stainless steel, which can withstand up to about 70 Newtons of axial load without breakage. The tensile strength of the retaining loop wire 2930 is preferably designed to range between 200 to 300 kpsi in order to accommodate for the 70 N load which may be created against retaining loop assembly 2891 by distal movement of the outer sheath 1200 relative to the inner catheter 1207. The first pair of cannulas 2902, 2904, the second cannula 2903 and the retaining loop wire 2930 may be formed from any other suitable biocompatible material known in the art.

Alternatively, the first pair of cannulas 2902 and 2904 and/or the second cannula 2903 may be formed from a high strength biocompatible polymeric material capable of withstanding the high loads which can occur during resheathing of outer sheath 1200. In a preferred embodiment using polymeric material, the first pair of cannulas 2902 and 2904 may be formed from polyetheretherketone (PEEK) and similar polymers.

Figure 29A:
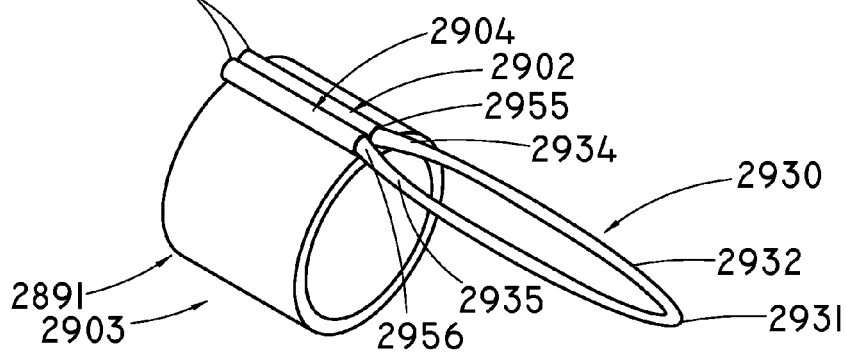
Figure 29B:
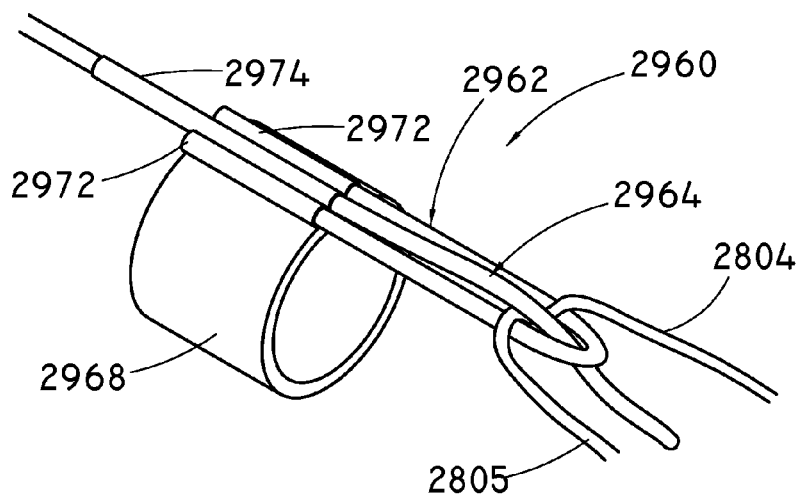

An alternate embodiment of an anchorage assembly 2960 including a retaining loop 2962 and a lockwire 2964 is shown in FIG. 29B. Engagement of the lockwire 2964 with the retaining loop 2962 retains the stent 2804 on the inner catheter 1207 during resheathing of the outer catheter 1200 and during deployment of the stent 2804. The anchorage assembly 2960 includes a first cannula 2968, a pair of retaining loop cannulas 2970, 2972 and a lockwire cannula 2974. The retaining loop wire 2962 may be inserted into the retaining loop cannulas 2970 and 2972 forming a loop and the lockwire 2964 may be extended through the lockwire cannula 2974 so that the lockwire 2964 extends past the retaining loop 2962 to releasably lock the retaining loop with the stent 2804. The lockwire 2964 may be woven over a strut 2805 of the stent 2804 and under the retaining loop wire 2962 as shown in FIG. 29B. Alternatively, the lockwire 2964 may be woven under a strut 2805 of the stent 2804 and over the retaining loop wire 2962. The pair of retaining loop cannulas 2970, 2972 and a lockwire cannula 2974 are shown connected to the first cannula 2968. The connection may be formed by any method known to one skilled in the art such as described above the first pair of cannulas 2902 and 2904. Because the retaining wire is connected only at the cannulas 2968, 2970, strain release of retaining loop wire 2962 occurs which enables substantial flexing of the loop wire 2962 without breakage.

Configuration of the retaining loop assembly 2891 relative to various sections of the inner catheter 1207 and outer catheter 1200 can be seen in FIG. 30. The anchorage assembly 2891 and the retaining loop assembly 2962 shown in FIG. 29B may be similarly configured relative to the sections of the inner catheter 1207 and the outer catheter 1200 as described below for the retaining loop assembly 2891. FIG. 30 is an expanded view of the distal portion of the device 100 disposed distal of the handle. FIG. 30 shows the outer sheath 1200 partially disposed over the inner catheter 1207. The distal region of the inner catheter 1207 as shown contains four sections. Section 1206 of inner catheter 1207 extends along the proximal direction into the handle of the device 100 and constitutes the majority of longitudinal length of inner catheter 1207. Section 1210 is the smallest diameter portion of the inner catheter 1207 and represents the region where stent 2804 is loaded therealong. Minimizing the diameter of inner catheter 1207 to that of section 1210 enables loading a larger diameter self-expandable stent 2804 which in turn provides a larger radial force when deployed at a target stricture. A sufficient radial force is necessary for self-expandable 2804 to maintain patency within the lumen of the target stricture and not migrate away from the stricture due to peristalsis effects which occur in the gastrointestinal tract. The proximal end of the section 1210 partially extends into section 1206 (e.g., about 15 mm) to ensure sufficient attachment there between. The stent 2804 (not shown) when loaded along section 1206 is compressed along section 1210 and abutted against the stent pusher section 1209, which is shown mounted over section 1206. Section 1208 represents the distal portion of section 1206. Section 1208 is flared outwards a sufficient amount to prevent distal movement of the second cannula 2903 of the retaining loop assembly 2891. Preferably, the size of the flare of the section 1208 is greater than the inner diameter of the second cannula 2903. However, other sizes of the cannula 2903 and the flare of the section 1208 may be used. Retaining loop assembly 2891 is disposed over section 1206 and abutted against flared section 1208 where it is affixed by any means known in the art, such as, for example, an adhesive. The flared section 1208 prevents the second cannula 2903 of retaining loop assembly 2891 from moving in the distal section towards stent pusher section 1209.

The retaining loop wire 2930 is shown in FIG. 30 to extend slightly distally of distal end of the pusher section 1209. Distal portion 2810 of lockwire 2802 is shown emerging from within the outer sheath 1200 and section 1206 of inner sheath 1207. The retaining loop wire 2930 is configured to be disposed within the lumen of stent 2804 as shown in FIG. 28. The distal portion 2810 of the lockwire 2802 is configured to emerge from within the outer sheath 1200 and section 1206 of inner catheter 1207 and engage with the retaining loop wire 2930 and strut 2805 of stent 2804 at anchorage points 2801, as shown in FIG. 28. The stent 2804 in its loaded configuration will be disposed over section 1210 of inner catheter and abutted against stent pusher section 1209 (FIG. 30).

Figure 32:
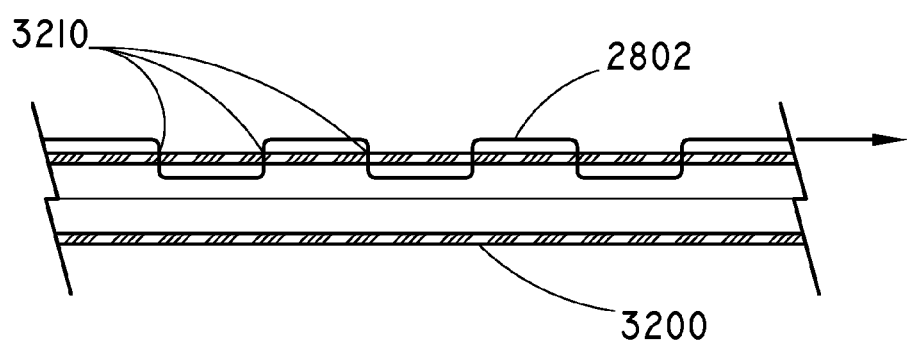
FIG. 32 shows a friction mechanism for preventing premature disengagement of lockwire from stent.

A frictional mechanism may be incorporated to prevent premature disengagement of the lockwire 2802 with the retaining loop wire 2930 and the strut 2806 at anchorage point 2801. In one example, as shown in FIG. 32, a static tube 3200 may serve as the frictional mechanism. The static tube 3200 is preferably disposed at the distal end of the handle of device 100 (FIG. 1) and coaxially between outer sheath 1200 and section 1206 of inner catheter 1207. FIG. 32 shows a side profile of an exemplary static tube 3200. The static tube 3200 has a predetermined longitudinal length. Any means may be used to affix static tube 3200 between outer sheath 1200 and section 1206 of inner catheter 1207, including, for example, an adhesive or a mechanical connector. A predetermined number of slits 3210 are created within the wall of static tube 3200 into which the lockwire 2802 loops or weaves in and out. This weaving of the lockwire 2802 increases the frictional force required for pulling the lockwire 2802 out from the slits 3210 of static tube 3200. Generally speaking, increasing the number of slits 3210 and increasing the longitudinal length of static tube 3200 along which the slits 3200 span therealong will tend to increase the frictional force required to completely pull lockwire 2802 out of static tube 3200. Accordingly, the static tube 3200 may substantially prevent the lockwire 2802 from inadvertently slipping proximally or distally between the inner catheter 1207 and the outer sheath 1200. In other words, the lockwire 2802 remains stationary at the anchorage point 2801 until it is intended to be proximally pulled therefrom. Such a frictional mechanism may be conducive when delivery and deployment of stent 2804 is occurring within tortuous body pathways.

Disengagement of the lockwire 2802 occurs when the stent 2804 is ready to be fully deployed at a target site within a body lumen. Directional switch 101 (FIG. 1) is pressed to actuate the second gear set 400 (FIG. 3) to enable proximal retraction of the outer sheath 1200 relative to the inner catheter 1207. With the second pulley gear 402 still mechanically coupled to the center drive pulley 901, trigger 102 is actuated multiple times to retract the outer sheath 1200 in the proximal direction relative to the inner catheter 1207 until the stent 2804 has fully radially expanded. The outer sheath 1200 is retracted in a proximal direction so as to fully expose the self-expandable stent 2804. At this juncture, the lockwire 2802 is disengaged from the strut 2806 of stent 2804 and from retaining loop wire 2930 (FIG. 28). FIG. 24 shows that the proximal portion of the lockwire 2802 extends proximally between the inner catheter 1207 and the outer sheath 1200 and terminates as a pigtail 2401 at the rear hub 104 of the handle of the device 100. The pigtail 2401 is pulled so as to remove lockwire 2802 in a proximal direction from anchorage point 2801. The lockwire 2802 is completely removed from device 100, thereby disengaging the stent 2804 from section 1210 (FIG. 30) of inner catheter 1207. At this juncture, the stent 2804 is completely deployed within the body lumen.

The stabilization embodiment described above in conjunction with FIGS. 28-32 provides many advantages described below with reference to the retaining loop assembly 2891 and also applicable to the alternate embodiments described herein. The retaining loop assembly 2891 does not substantially increase the lateral profile of outer catheter 1200 and inner catheter 1207, thereby enabling through the scope (TTS) self-expandable stents, such as duodenal and colonic stents, to be advanced through an endoscopic accessory channel, which typically has a diameter of about 3.7 mm or less. Additionally, the retaining loop assembly 2891 is designed and constructed to withstand the large axial loads (FIG. 31), which can be incurred during resheathing of stent 2804, without breakage of retaining loop wire 2930 or detachment of second cannula 2903 from section 1206 of inner catheter 1207 (FIG. 30). Additionally, the retaining loop wire 2930 is shown anchored to stent 2804 more proximally compared to the bilumen tubing 291 stabilization element, thereby allowing a smaller lateral profile of inner catheter 1207 in the region that the stent 2804 is loaded. Incorporation of the static tube 3200 described above also prevents premature disengagement of the stabilization elements. Particularly, the static tube 3200 enables lockwire 2802 to remain stationary at the anchorage point 2801 to fixate the stent 2804 to inner catheter 1207 until the stent 2804 is intended to be fully deployed and therefore disengaged from inner catheter 1207.

A delivery device 4000 is shown in FIG. 39A in a short wire configuration including an inner catheter 4010, an outer sheath 4012 and an exchange port 4014 at a distal portion 4016 of the delivery device 4000. A guide wire 4018 is insertable through the exchange port 4014 at the distal portion 4016 and exits the delivery device 4000 through a distal port 4020. The short wire configuration of the delivery device 4000 allows the guide wire 4018 to be inserted into the exchange port 4014 that is distal to a handle entry port used in an over-the-wire configuration described above. The delivery device 4000 is configured to allow the guide wire 4018 to exit the distal port 4020 in a direction that is substantially parallel to a main axis 4022 of the delivery device 4000 to improve trackability and delivery through an endoscope that is difficult when the guide wire 4018 is provided at an angle to main axis 4022. The delivery device 4000 is provided with a handle 4024 at a proximal portion 4026. The handle 4024 may function similarly to the embodiments described above and shown for example in FIGS. 1-12. A retaining wire (not shown) similar to the embodiments described above may also be used with the delivery device 4000 that is insertable through the handle 4024 and provided to releasably hold a stent 4004 to the inner catheter 4010. An enlarged view of the distal portion 4016 of the delivery system 4000 is shown in FIG. 39B, where the stent 4004 is positioned on the inner catheter 4010 and the guide wire 4018 is shown inserted into the exchange port 4014 and exiting the distal port 4020.

Figure 40A:
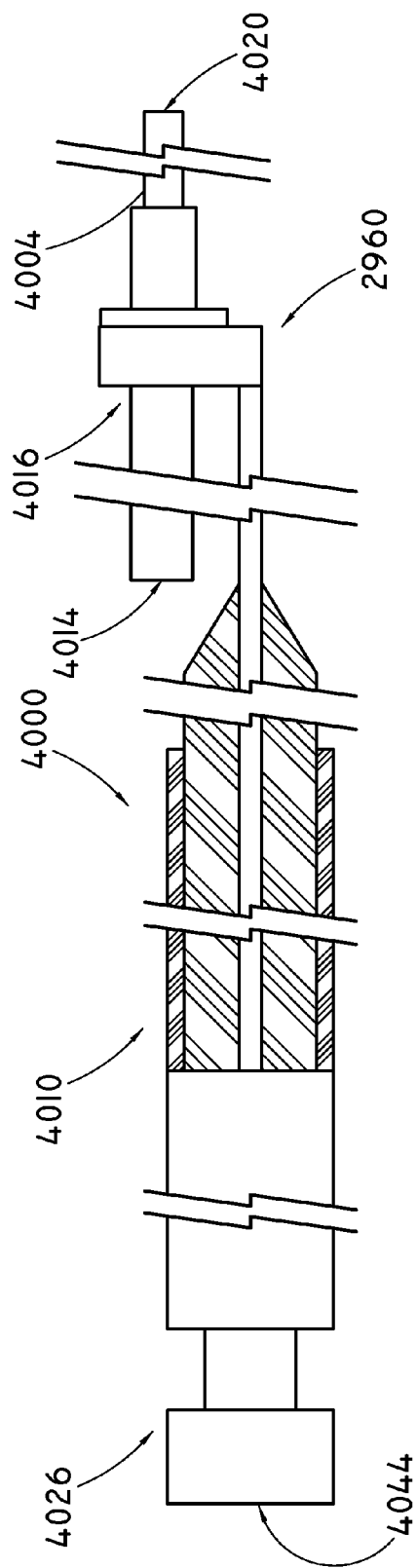
Figure 40B:
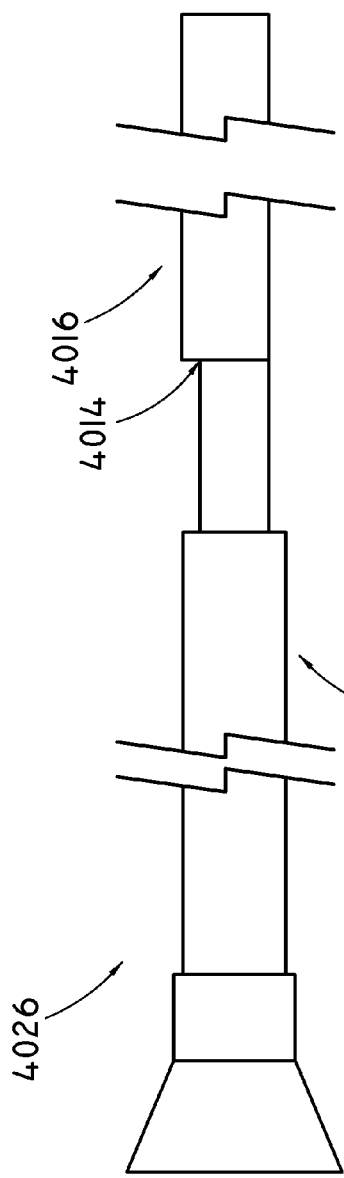

FIGS. 40A and 40B illustrate embodiments of the inner catheter 4010 and the outer sheath 4012, respectively, of the short wire configuration for the delivery device 4000. A lockwire port 4044 is shown at the proximal portion 4026 of the delivery device 4000 and the exchange port 4014 and distal port 4020 are shown at the distal portion 4016. The inner catheter 4010 may include an anchorage assembly at the distal portion 4016, such as the anchorage assembly 2960 as shown in FIG. 29B, to hold the stent 4004 to the inner catheter as the outer sheath 4012 is proximally withdrawn and distally replaced over the stent. The outer sheath 4012 having a short wire configuration with the distal exchange port 4014 is shown in FIG. 40B. The guide wire 4018 may be inserted into the exchange port 4014 in the outer catheter 4012 and the inner catheter 4010 and out of the distal port 4020. Similar to the embodiments described above, the stent 4004 may be resheathed by the outer catheter 4012 while the stent 4004 is held in position over the inner catheter 4010 by the anchorage assembly 2960.

Delivery of TTS self-expandable stents for deployment within the gastrointestinal tract necessitates that the outer sheath and inner catheter be sufficiently small in size to fit through an accessory channel of an endoscope. Additionally, because the tumor within the gastrointestinal tract is often situated in difficult-to-access regions (e.g., ascending colon or duodenum), the outer sheath and inner catheter should be sufficiently flexible but yet kink resistant and pushable to navigate to these difficult-to-access regions. Notwithstanding these desirable attributes of the outer sheath and inner catheter, the extent to which the lateral profile of the outer sheath may be decreased will be limited by the radial force the TTS self-expandable stent is required to exert at the target stricture. Outer sheaths which are too thin may not have sufficient mechanical strength to deploy a TTS stent because the TTS stent needs to exert a radial force sufficient to maintain patency at the stricture and remain anchored therewithin so as to be resistant to any tendency to migrate away from the stricture due to peristalsis effects. Therefore, generation of sufficient radial force at a target stricture requires deploying a TTS stent with the largest possible radial force. Accordingly, thin sheaths may experience higher stress levels during deployment (i.e., the forces required at the handle of the device 100 to proximally pull the outer sheath 1200 relative to inner catheter 1207 to fully expose the stent 2804) and during resheathing (i.e, the forces required at the handle of the device 100 for distally pushing the outer sheath 1200 relative to the inner catheter 1207 to fully reheat the inner catheter 1207) compared to larger sheaths. The higher forces required for resheathing or deployment of outer sheath can be burdensome. Although larger sized outer sheaths would be favorable to decrease such forces, the outer diameter of the outer sheath is limited by the size of the accessory channel on the endoscope and reducing the inner diameter of the outer sheath limits the amount of radial force of a TTS stent that can be loaded and deployed. As mentioned, large radial forces are required to maintain patency of a target stricture and prevent migration of the stent due to peristalsis effects occurring in the gastrointestinal tract.

Accordingly, an outer sheath is preferably selected so as to achieve a balance between the above described limitations. FIGS. 33-36 depict a reinforced outer sheath 3300. The outer sheath 3300 preferably spans a longitudinal length sufficient to deploy a TTS stent into the gastrointestinal tract. In one example, the longitudinal length of the outer sheath 3300 is about 240 centimeters. The outer sheath 3300 includes proximal reinforced section 3301 and a distal reinforced section 3302. The proximal reinforced section 3301 is shown in FIG. 33 to extend from a distal end of the handle 110 of device 100 and comprises about 90% of the overall longitudinal length of the reinforced outer sheath 3300. The proximal reinforced section 3301 is reinforced by a braid 3316 which extends throughout the entire proximal reinforced section 3301. The distal reinforced section 3302 comprises about 10% of the overall longitudinal length of the reinforced outer sheath 3300 and is defined as the region of the sheath 3300 within which a self-expandable stent 2804 (not shown) can be disposed. The distal reinforced section 3302 is reinforced by a coil 3314. The coil 3314 is preferably configured in a radially expanded condition and longitudinally extends along distal reinforced section 3302 and subsequently terminates at a distance away from distal tip 3366 (FIG. 33).

FIG. 35 shows an expanded view of the proximal reinforced section 3301. FIG. 35 shows that the proximal reinforced section 3301 comprises an outer layer 3318 and an inner layer 3319. The braid 3316 is embedded between the outer layer 3318 and the inner layer 3319. The braid 3316 is shown to comprise the multiple crossed wires 3317 of circular cross-sectional shape. The braid 3316 may also comprise multiple crossed wires 3317 of any cross-sectional shape. The wires 3317 may be formed from several types of gauge material having various cross sectional shapes. Suitable dimensions of wires 3317 may vary depending on the particular application. In a preferred embodiment, the wires 3317 are formed from 0.003" gauge stainless steel ASTM 302 or 304 round wire having a minimum tensile strength of 128 kPSI. Other medical grade materials are contemplated and may also be useful for the wires 3317. For example, the wires 3317 of braid 3317 may be formed from a shape memory metallic alloy.

The outer layer 3318 contacts the braid 3316 as shown in FIG. 35. The outer layer 3318 preferably is formed from a polymeric material, such as polyurethane or nylon, which is preferably of a relatively higher durometer than the outer layer 3303 of the distal section 3302 (FIG. 34). The higher durometer provides increased resistance to stretching, which may be especially problematic when proximal section 3301 is being navigated through tortuous body lumens. In a preferred embodiment, the outer layer 3318 comprises nylon. The nylon outer layer 3318 preferably comprises blue color pigment which enhances its visibility when viewed under an endoscope. Braid 3316 in combination with the higher durometer nylon outer layer 3318 may increase the column strength of the proximal section 3301 relative to non-reinforced sheaths. The relatively increased column strength improves pushability and flexibility while reducing kinking of the proximal section 3301 during navigation to a target stricture. Inner layer 3319 is preferably formed from a lubricious material such as polytetrafluoroethylene (PTFE). The lubricious inner layer 3319 creates a slippery surface along the inner diameter of reinforced outer sheath 3300 which may facilitate proximal and distal movement of reinforced outer sheath 3300 relative to inner sheath 1207 during resheathing or complete deployment of stent 2804. Other medical grade lubricious materials known in the art are also contemplated.

FIG. 34 shows that the distal reinforced section 3302 comprises an outer layer 3303 and an inner layer 3304. The coil 3314 may be formed from multiple wires. Preferably, the coil 3314 is formed from a single wire wound in a helical manner. The coil 3314 comprise multiple flat wire elements 3310 (shown in cross section in FIG. 34), and is preferably formed from a medical grade metal alloy, such as, for example, shape memory metal alloys. In a preferred embodiment, the coil 3314 may be formed from 0.003" thick by 0.012" wide flat rectangular ASTM 302 or 304 stainless steel wire which is wound with a substantially constant spacing between the flat wire elements 3310. The spacing is preferably sufficient so that the sheath 3300 along the distal reinforced section 3302 is at least semi-transparent to enable the stent to be visible within the distal section 3302. The coil 3314 may comprise a suitable helical pitch of about 0.045 inches, plus or minus 0.005 inches. The coil 3314 preferably does not extend to the distal edge of distal section 3302. Rather, the coil 3314 terminates proximal to the distal tip 3366 as shown in FIG. 33 to ensure that the coil 3314 does not become exposed beyond the distal end of distal tip 3366. The flat wire elements 3310 are embedded between the outer layer 3303 and the inner layer 3304. The outer layer 3303 is shown in FIG. 35 to be positioned over and contacting the flat wire elements 3310. The outer layer 3303 preferably maintains the flat wire elements 3310 of coil 3314 in at least a partially radially expanded and stressed configuration between the outer layer 3303 and inner layer 3304. In a preferred embodiment, the outer layer 3303 is affixed to the flat wire elements 3310 of coil 3314 by adhesion, such as, for example, by thermal bonding to the flat wire elements 3310. Although coil 3314 is shown as having rectangular shaped flat wire elements 3310, other shapes of flat wire elements 3310 are contemplated and may be utilized.

The outer layer 3303 preferably is formed from a polymeric material, such as nylon, which is preferably of a relatively lower durometer than the outer layer 3318 of the proximal section 3301. Making the distal section 3302 of outer layer 3303 from a relatively lower durometer nylon as compared to the proximal section 3301 creates a reinforced outer sheath 3300 having a distal section 3302 and distal tip 3366 that is more flexible than the proximal section 3301. The nylon outer layer 3303 preferably comprises a transparent pigment which enables the stent 2804 to be visible within the distal section 3302 through the endoscope.

Inner layer 3304 is preferably formed from a lubricious material such as polytetrafluoroethylene (PTFE). The lubricious inner layer 3304 creates a slippery surface which facilitates loading and deployment of stent 2804 between the reinforced outer sheath 3300 and section 1210 of inner catheter 1207 along distal section 3302. In other words, the inner PTFE liner of sheath 3300 reduces the force needed to proximally and distally move outer sheath 3300 relative to inner sheath 1207. Other medical grade lubricious materials known in the art are also contemplated.

The reinforced coil 3314 disposed along distal section 3302 (FIG. 34) provides several benefits. The coil 3314 is designed with a predetermined number of windings per length which provides increased hoop strength of the distal section 3302 compared to non-reinforced sheaths. Hoop strength as used herein refers to the ability of the distal section 3302 of sheath 3300 to maintain its structural integrity and resist deformation incurred by the relatively high radial forces imparted by a loaded TTS stent within the distal section 2804. The hoop strength of coil 3314 may also reduce the deployment forces generated during resheathing and/or stent deployment operations. Specifically, the increased hoop strength provided by coil 3314 reduces the tendency for loaded TTS stent to bite into the wall of the reinforced outer sheath 3300, thereby reducing the deployment and resheathing forces compared to non-reinforced sheaths. The increase in hoop strength of sheath 3300 contributed by coil 3314 may be significant. The absence of the coil 3314 would require increasing the wall thickness of the sheath 3300 along the distal section 3302 to such an extent that the profile of sheath 3300 would be too large to fit within a conventional endoscopic accessory channel having a diameter of about 3.7 mm or less. Additionally, the structure of coil 3314 enables advancement of distal section 3302 through tortuous body lumens. Specifically, the helical windings of coil 3314 along distal section 3302 enable section 3302 of outer sheath 3300 to contour into various tortuous positions of such body lumens without undergoing significant kinking.

FIG. 36 shows that that the flatwire elements 3610 of coil 3314 overlap a predetermined amount into the proximal section 3301. Overlap section 3303 represents a longitudinal portion of reinforced outer sheath 3300 along the proximal section 3301 that comprises both the coil 3314 and the braid 3316. The overlap section 3301 may be any length to ensure sufficient anchorage. In one example, the overlap section 3301 is about 1 cm. The attachment of the proximal portion of coil 3314 with the distal portion of braid 3316 may be achieved in numerous ways, including adhesion or mechanical affixation. The overlap of coil 3314 with braid 3316 at overlap section 3303 ensures sufficient anchorage between the two such that there are no weak points along outer sheath 3300. The overlap section 3303 comprises physical properties of both the proximal section 3301 that is reinforced with braid wire 3316 and the distal section 3302 that is reinforce with coil 3314. Failure to create such an anchorage of braid 3316 and coil 3314 at overlap section 3303 may create a gap along the outer sheath 3300 in which no coil 3314 or braid 3316 exists, thereby creating a weak point which may be subject to kinking or subject to damage. The overlap section 3303 also helps to facilitate a gradual transition in physical properties from the proximal section 3301 to the distal section 3302. As shown in FIG. 36, the coil 3314 is wound around the braid 3316 at overlap section 3303. Alternatively, the braid 3316 may be wound around the coil 3314 at the overlap section 3303.

Assembly of reinforced outer sheath 3300 preferably occurs over a mandrel. The PTFE inner liner 3319 of proximal section 3301 (FIG. 35) and PTFE inner liner 3304 of distal section 3302 (FIG. 34) are preferably a single piece of material extending along the length of the outer sheath 3300. The PTFE is placed over the mandrel. Next, the braid 3316 is slid over the PTFE. The braid 3316 is positioned over the mandrel at the proximal section 3301 of the outer sheath 3300. The coil 3314 is also slid over the mandrel. The coil 3314 is positioned such that a proximal end 3377 (FIG. 36) of the coil 3314 overlaps (e.g., about 1 cm) into the proximal portion 3301 where the braid 3316 is disposed to create the overlap section 3303. The nylon outer layer 3318 of proximal section 3301 is slid onto the proximal section of the mandrel and the nylon outer layer 3303 of distal section 3302 is slid onto the distal section of the mandrel. A heat shrinkable tubing may then be disposed over all of these components which are now positioned as desired over the mandrel. The mandrel and the components disposed thereon are heated to a temperature sufficient to shrink and cure the heat shrinkable tubing, thereby causing it to thermally bond over the braid 3316 and coil 3314. The inner PTFE liner, coil 3314 and braid 3316 reinforcement components, and outer nylon layers 3303 and 3318 become thermally fused to each other. The mandrel and newly formed reinforced outer sheath 3300 are then ambient cooled, and the heat shrinkable tubing is removed from the mandrel.

Although the proximal section 3301 and distal section 3302 have been described as being reinforced with braid 3316 and coil 3314 respectively, it should be understood that other means for achieving the desired properties (e.g., enhanced flexibility, tensile strength, hoop strength, column strength, and kink resistance) in each of the sections 3301 and 3302 are contemplated. For example, the proximal and distal sections 3301 and 3302 may comprise different composites of outer materials with varying thicknesses which are individually fabricated and thereafter joined to exhibit the desired physical properties and transition in properties as needed from proximal region of outer sheath to an overlapping section to distal region of outer sheath.

Although the above described reinforced sheath 3300 has been described for delivery and deployment of stents into the colonic and duodenal regions, other TTS stents may be deployed. Additionally, the reinforced sheath 3300 may be modified for suitable use with non-TTS stents. For example, the sheath 3300 may be used to deliver and deploy an esophageal stent.

Figure 22:
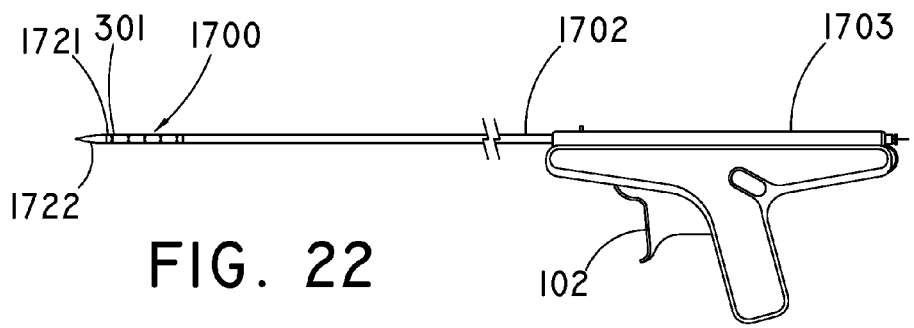
FIG. 22 shows the entire delivery device preloaded with an esophageal stent at the distal tip of the delivery section.

Having described the structure of the device 100 and the operation of the device 100 (i.e., the internal gear mechanism to retract/resheath the outer catheter 1200) and the various stabilization elements to fixate the stent 301 during the resheathing process, a method of use of the device 100 may now be described. The device 100 may be used to deploy various prostheses. As an example, a method of deploying an esophageal stent 301 will now be described. The esophageal stent 301 is loaded in between the inner catheter 1207 and the outer catheter 1200 along the distal end 1700 of the device 100, as shown in FIG. 22. Part of the loading process of the stent 301 involves affixing retaining wire 290 from one of the crowns 300 at the proximal end of the stent 301 to the rear hub 104 located at the proximal end of the device 100, as was described and shown in FIGS. 13-16.

Figure 41A:
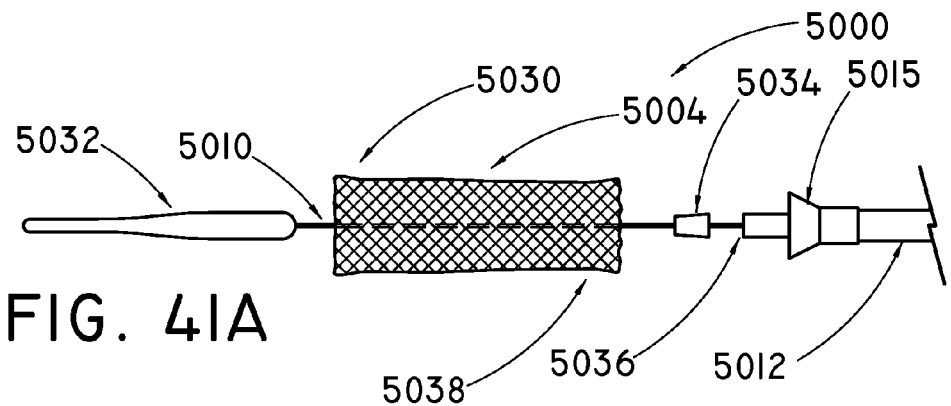
FIGS. 41A-41C show an embodiment of a delivery system for a stent having delayed loading characteristics.
Figure 41B:
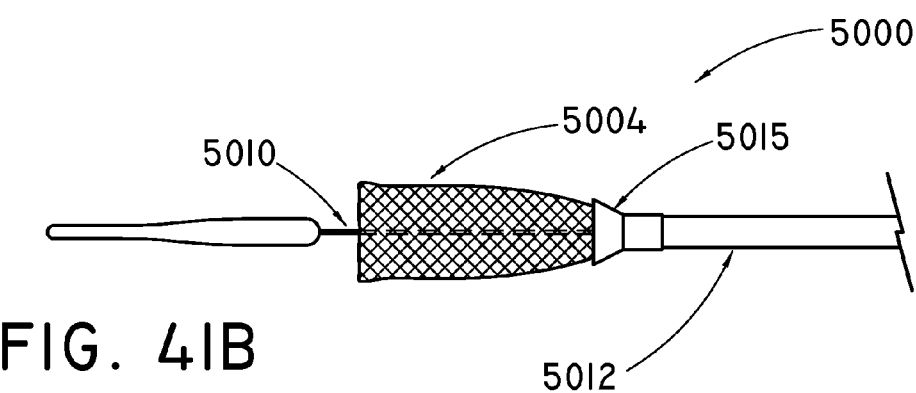
Figure 41C:
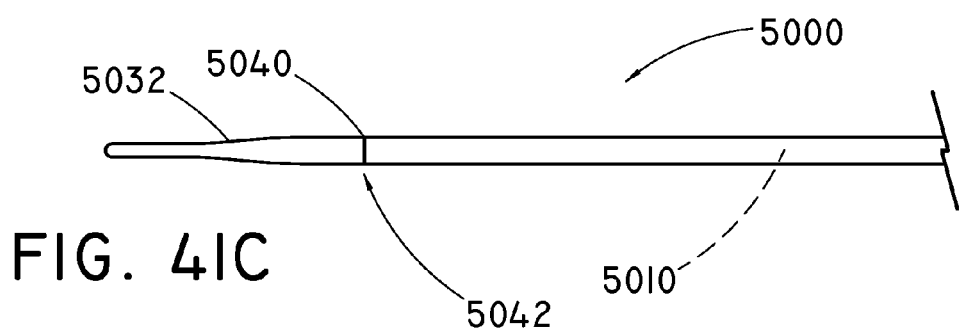

In some embodiments, a stent 5004 provided for use with any of the delivery systems described above may be loaded into the delivery system just prior to insertion of the stent 5004 into the patient. By way of non-limiting example, the stent 5004 may be a biodegradable stent having properties that prevent the stent 5004 from being preloaded into the delivery system at the manufacturer and stored in a compressed configuration. An exemplary embodiment of a delivery system 5000 is shown in FIG. 41A for use with the stent 5004 that is loaded onto the delivery system 5000 at the time of the patient procedure. The delivery system 5000 is similar to the delivery systems described above and includes a funnel shaped member 5015 for loading the stent 5004 positioned around an inner catheter 5010 into an outer sheath 5012. As shown in FIG. 41A, the stent 5004 is in an expanded configuration 5030 around the inner catheter 5010 and positioned between a distal tip 5032 and a holder device 5034. The delivery system 5000 may also include a pusher catheter 5036 proximal to the holder device 5034. A proximal portion 5036 of the stent 5004 may be collapsed around the holder device 5034 and the proximal portion 5036 of the stent 5004 proximally drawn toward the funnel shaped member 5015. A partially collapsed stent 5004 is shown in FIG. 41B with the proximal portion 5036 withdrawn into the outer sheath 5012. A handle similar to the embodiments described above for moving the inner catheter relative to the outer sheath may be used to move the inner catheter 5010 and the outer sheath 5012 axially relative to each other to position the outer sheath 5012 over the stent 5004. FIG. 41C illustrates the stent 5004 fully loaded into the delivery system 5000 with a distal end 5040 of the sheath 5012 abutting the distal tip 5032 of the inner catheter 5010 to form a smooth outer surface 5042. The funnel 5015 is removed from the delivery system 5000 with the stent 5004 fully loaded and ready to be delivered to the patient as shown in FIG. 41C. In operation of the delivery device 5000, the holder device 5034 may be used to hold the proximal portion 5036 of the stent 5004 between the inner catheter 5010 and the outer sheath 5012 as the outer sheath 5012 is proximally withdrawn to expose the stent 5004 at the patient delivery site. Similar to the preloaded stents described above, the stent 5004 may be resheathed with the outer sheath 5012 when up to about 90-95% of the stent 5004 has been unsheathed. The holder device 5034 may be used to retain the remaining 5-10% of the proximal portion 5036 of the stent 5004 under constraint by the outer sheath 5012.

The delivery system 5000 may also be provided with an anchorage assembly 5048 as shown in FIGS. 42A and 42B releasably holding the stent 5004 to the inner catheter 5012. The anchorage assembly 5048 may include a proximal suture loop 5050 and/or a proximal locking wire 5052 as shown in FIGS. 42A and 42B. The delivery system 5000 may also be provided with a distal suture loop and/or locking wire (not shown) that operate similarly to the proximal suture loop 5050 and/or the proximal locking wire 5052. One skilled in the art will also understand that the delivery system 5000 may also be provided with an anchorage assembly including a retaining loop as described above for releasably holding the stent 5004 to the inner catheter 5012.

As shown in FIG. 42A, the stent 5004 may be provided in the expanded configuration 5030 to be collapsed onto the inner catheter 5010 just before the stent 5004 is delivered to the patient. The stent 5004 may be stored and shipped in the expanded configuration 5030 and held to the inner catheter 5010 during that time using the anchorage assembly 5048 including a suture loop 5050 woven through the stent 5004 to loosely hold the stent 5004 on the inner catheter 5010. An enlarged view of the anchorage assembly 5048 without the stent is shown in FIG. 42B including the lockwire 5052 that will be woven between the stent 5004 and the suture loop 5050 for delivery. The suture loop 5050 may be fixed to the inner catheter 5010 or the optional pusher catheter 5036 as shown in FIG. 42B. The suture loop 5050 may also be provided through a lumen within the delivery system 5000 and connected to the stent 5004. The funnel 5015 is included and a proximal portion 5056 of the funnel 5015 is temporarily positioned at the distal end 5040 of the outer sheath 5012. The proximal portion 5056 of the funnel 5015 may be sized so that the proximal portion 5056 is slightly small than the distal end 5040 of the outer sheath 5012 so that the outer sheath 5012 slides over the proximal portion of the stent 5004 as the inner catheter 5010 and the outer sheath 5012 are moved axially relative to each other. The anchorage assembly 5048 may be used to hold the stent 5004 in position as the stent 5004 is covered by the outer sheath 5012. In this embodiment, the stent 5004 may be repeated sheathed and unsheathed. The anchorage assembly 5048 may be released from the stent once the stent is covered by outer sheath or later, when the stent 5004 is ready for complete deployment within the patient. For example, the lockwire 5052 may be connected to a handle 5060 at a proximal portion 5062 of the delivery device 5000. The lockwire 5052 may be proximally withdrawn to release the stent 5004 from the suture loop 5050 and the inner catheter 5010.

Figure 23:
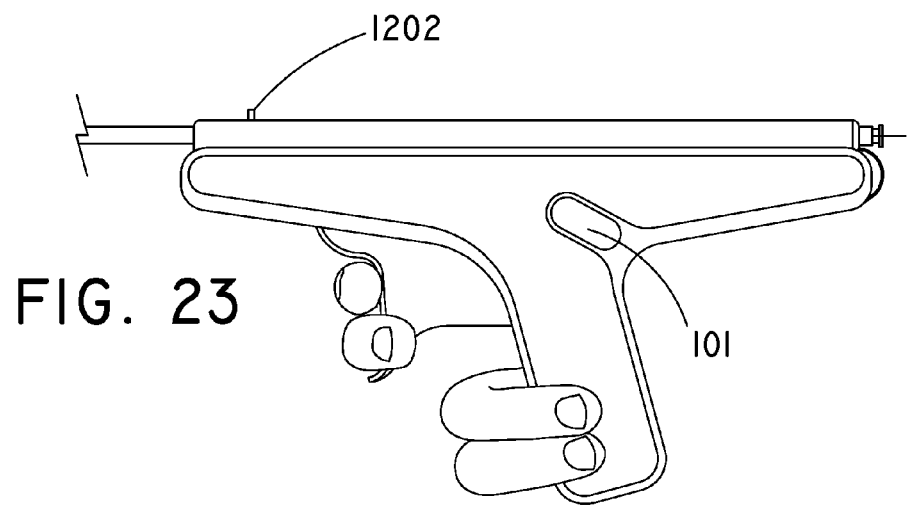
FIGS. 23-26 show a method of use of the delivery device.
Figure 25:
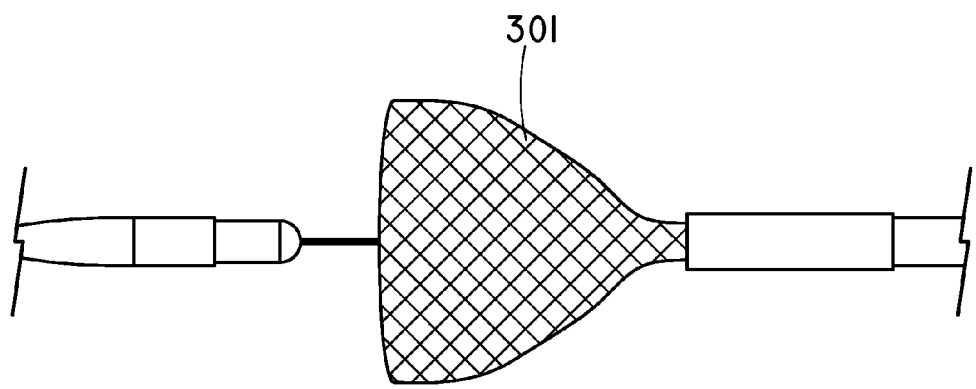
Figure 26:
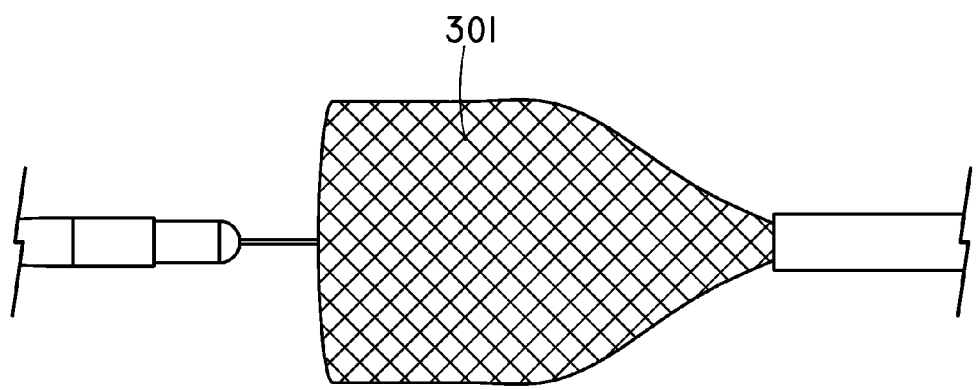

Delivery and deployment are described below with reference to the stent 301, however, one skilled in the art will understand that the delivery and deployment methods are also applicable to other embodiments described herein. Having loaded the esophageal stent 301 and affixed the retaining wire 290 to the esophageal stent 301, the delivery and deployment process may begin. The delivery device 100 comprises a stent delivery section 1702 and an external manipulation section 1703. The delivery section 1702 travels through the body lumen during the procedure and delivers the prosthesis to a desired deployment site within the esophagus. The external manipulation section 1703 stays outside of the body during the procedure. The external manipulation section 1703 includes trigger 102 and can be manipulated by the physician with a single hand (FIG. 23) to position and release the stent 301 into the body lumen. After having delivered the delivery section 1702 of the delivery device 100 to the target site within the esophagus, the deployment of the stent 301 may begin. The trigger portion 102 of the device 100 will remain outside of the patient to enable deployment of the esophageal stent 301. The physician presses the directional switch 101 to actuate the second gear set 400 (FIG. 3) to enable proximal retraction of the outer catheter 1200 relative to the inner catheter 1207. FIG. 23 indicates that the shuttle 1202 is positioned near the distal end of the external manipulation section 1703. Having pressed the directional switch 101 to actuate the second gear set 400 with the center drive pulley 901, the physician may grasp the trigger 102 of the device 100 with a single hand, as shown in FIG. 23, to actuate the trigger 102 for the first time. The other hand may be free to perform other tasks. FIG. 24 indicates that the trigger 102 has been completely pulled backed in the proximal direction. In particular, the tip of the shuttle 1202 has proximally moved after one actuation of the trigger 102. With the second pulley gear 402 still mechanically coupled to the center drive pulley 901, trigger 102 is actuated multiple times to retract the outer catheter 1200 in the proximal direction relative to the inner catheter 1207 until a portion of the esophageal stent 301 has become exposed and partially radially expanded, as shown in FIG. 25. Further actuations of the trigger 102 cause the outer sheath 1200 to proximally move back even further, thereby exposing an increasing portion of the self-expanding stent 301, as shown in FIG. 26.

At this juncture, notwithstanding partial radial expansion of the stent 301, the device 100 may be activated to resheath the outer catheter 1200 over the stent 301 to allow repositioning of the stent 301 within the esophagus. The physician may need to resheath and reposition the stent 301 as a result of having placed the stent 301 in the incorrect position. The directional switch 101 may be pressed to disengage the center drive pulley from the second pulley gear and to engage the center drive pulley with the first pulley gear (FIG. 8A). Having activated the first gear set 500 with the center drive pulley 901, actuation of the trigger 102 one or more times enables the outer sheath 1200 to move distally and resheath over the stent until the stent 301 is fully constrained back within the outer sheath 1200. With the stent 301 fully recaptured within the outer catheter 1200, the external manipulation section 1703 may be maneuvered to reposition the delivery section 1702 within the body lumen. After repositioning the delivery section 1702, the directional switch 101 may be reconfigured to reactivate the second gear set 400 with the center drive pulley 901 such that proximal retraction of the outer sheath 1200 occurs, thereby exposing the stent 301. The retaining wire 290 retains the stent 301 and prevents it from moving distally during resheathing.

Referring to FIG. 22, during deployment, the distal end 1700 of the outer catheter 1200 may comprise a transparent or translucent material (or a light-transmitting material) to enable the physician to visually observe the stent 301 and how it is positioned in relation to the esophageal stricture. FIG. 17 shows that the top-most portion of the shuttle 1202 protrudes through the housing of the device 100. The top-most portion of the shuttle 1202, as shown in FIG. 17, proximally moves back as the outer catheter 1200 is proximally retracted and may be used as a visual indicator to determine when resheathing capabilities have been lost. The distance that the top-most portion of the shuttle 1202 proximally moves back corresponds to the distance that the outer catheter 1200 has proximally retracted. The top-most portion of the shuttle 1202 can proximally move back a predetermined threshold distance beyond which the physician will realize that the outer catheter 1200 cannot be proximally retracted any further without losing the ability to resheath and recapture the stent 301 within the outer catheter 1200. Alternatively, the point at which the top-most portion of the shuttle 1202 aligns with a predetermined visual marker on the outer housing of the device 100 can also indicate the loss of the ability to resheath.

In an alternative embodiment, one or more radiopaque markers 1721 may be used under fluoroscopy to determine the distance the outer catheter 1200 has proximally retracted (FIG. 22). The radiopaque marker 1721 may be placed on the outer catheter 1200 between the distal tip 1722 and the distal end 1700 of the clear portion of the outer catheter 1200, as shown in FIG. 22. The one or more markers 1721 may be utilized to determine when the resheathing capabilities have been lost. For example, as the outer catheter 1200 is proximally retracted, the radiopaque marker 1721 may move along with it. The marker on the inner catheter 1207 (FIG. 1) may be positioned such that if the marker 1721 on the outer catheter 1200 aligns with the marker on the inner catheter 1207, the physician will realize that the stent 301 cannot be exposed any further without losing the ability to resheath and recapture the stent 301 within the outer catheter 1200.

As can be seen, the device 100 is capable of incrementally deploying the stent 301. In the above examples described, one full actuation of the trigger 102 may proximally move the belt 1201 and hence the outer sheath 1200 from about 5 mm to about 10 mm. Such incremental deployment may facilitate greater accuracy in positioning of the stent 301 at the target region. On the contrary, a conventional push-pull delivery device has less control as compared to the delivery device 100 because the conventional push-pull delivery device cannot withdraw the outer sheath in such small, precise increments. Conventional push-pull delivery devices require the user to maintain one portion of the handle in a fixed position and manually either pull in a proximal direction relative to the fixed portion of the handle or push in a distal direction relative to the fixed portion of the handle to resheath the stent. The speed and control of the pulling and pushing of such conventional push-pull delivery devices is wholly dependent on the user, thereby preventing deployment in the small, precise increments which device 100 can perform. Additionally, stents with low or high deployment forces may contribute to the lack of control of push-pull delivery devices. The lack of control may result in sudden proximal movement of the outer sheath of about 50 mm or more, resulting in inaccurate placement of the deployed stent.

Another advantage of the device 100 as has been described is the ability to resheath the outer catheter 1200 over the stent 301. The resheathing feature gives the physician the ability to make real-time adjustments during the deployment procedure such that the stent may be repositioned. In the examples described, the stent 301 may be able to be resheathed even after about 10% of the stent 301 has been deployed or as much as about 95% of the stent 301 has been deployed. Yet other advantages include the ability to use a single hand to deploy the stent 301. The other hand may be free to perform other tasks, such as holding an endoscope when deploying a self-expandable stent therethrough.

The above described deployment and resheathing methods may also be utilized for TTS stents such as colonic or duodenal stents. Deployment or resheathing of such TTS stents would preferably involve using reinforced outer sheath 3300 (FIGS. 33-36) in place of outer sheath 1200 and the retaining loop assembly 2891 and lockwire 2802 (FIGS. 28-32) in place of the bilumen tubing/suture wire described in FIGS. 13-16.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. Furthermore, the advantages described above are not necessarily the only advantages of the invention, and it is not necessarily expected that all of the described advantages will be achieved with every embodiment of the invention.

The invention claimed is:

1. A delivery device for delivering an intraluminal device, comprising:
   an intraluminal device;
   a gear and pulley mechanism comprising a first gear set and a second gear set;
   a drive pulley adapted to be alternatively mechanically coupled to the first gear set and the second gear set, an outer sheath disposed over an inner elongate member, the sheath being in mechanical communication with the drive pulley so as to retract in a proximal direction and resheath in a distal direction; and
   a stabilizing element comprising an anchorage assembly, the anchorage assembly comprising a retaining loop assembly positioned on the inner elongate member and a lockwire, wherein engagement of a distal portion of the lockwire with the retaining loop assembly anchors the intraluminal device to the inner elongate member during movement of the outer sheath relative to the inner elongate member so that in an engaged position of the anchorage assembly, the retaining loop assembly and a portion of the intraluminal device overlap and the lockwire passes through the overlapping retaining loop assembly and the portion of the intraluminal device.

2. The delivery device of claim 1, wherein the outer sheath comprises a proximal section reinforced with a braid, a distal section reinforced with a coil and an overlapping section extending between the proximal section and the distal section, the overlapping section comprising a proximal portion of the coil affixed to a distal portion of the braid, the coil is disposed between an outer layer and an inner layer of the distal section of the outer sheath in at least a partially radially expanded state, the outer sheath being in mechanical communication with the drive pulley so as to retract in a proximal direction and resheath in a distal direction.

3. The delivery device of claim 2, wherein the inner layer comprises a lubricious liner extending from the proximal section to the distal section.

4. The delivery device of claim 2, wherein the proximal reinforced section comprises a first outer polymeric layer and the distal reinforced section comprises a second outer polymeric layer, the first outer polymeric layer having a higher durometer than that of the second outer polymeric layer.

5. The delivery device of claim 4, wherein the first and the second outer polymeric layers comprise nylon or polyurethane.

6. The delivery device of claim 2, wherein the braid comprises a plurality of crossed wires.

7. The delivery device of claim 2, wherein the coil comprises a flat rectangular wire.

8. The delivery device of claim 2, wherein the coil is configured to increase hoop strength to reduce deployment forces as compared to that of non-reinforced delivery sheaths.

9. The delivery device of claim 3, wherein the braid is embedded between an outer layer and an inner layer of the proximal section of the outer sheath, the braid configured to increase column strength to enhance pushability and flexibility and reduce kinking as compared to non-reinforced delivery sheaths.

10. The delivery device of claim 2, wherein the overlapping section is proximal to a location at which the outer sheath transitions from an opaque colored outer sheath to a transparent colored sheath.

11. The delivery device of claim 1, the retaining loop assembly further comprising a first pair of cannulas affixed to a second cannula and a retaining loop wire comprising a distal loop portion and a first proximal end and a second proximal end, the first and the second proximal ends inserted with the first pair of cannulas.

12. The delivery device of claim 1, wherein the anchorage assembly is configured to withstand about 70 Newtons of axial load.

13. The delivery device of claim 1, further comprising a static tube disposed distal to a handle of the delivery device, the static tube comprising a plurality of slits along a longitudinal length of the static tube, the slits being configured to receive a proximal portion of the lockwire so as to create a weaving of the lockwire into and out of the slits.

14. The delivery device of claim 1, wherein an overall diameter of the outer sheath, inner elongate member, and anchorage assembly is less than about 3.7 mm.

15. The delivery device of claim 1, wherein the intraluminal device is a through-the-scope (TTS) stent.

16. A delivery device for delivering an intraluminal device comprising:
    a gear and pulley mechanism comprising a first gear set and a second gear set;
    a drive pulley adapted to be alternatively mechanically coupled to the first gear set and the second gear set;
    a reinforced outer sheath disposed over an inner elongate member, the reinforced outer sheath comprising a proximal reinforced section and a distal reinforced section wherein the reinforced outer sheath is in mechanical communication with the drive pulley so as to retract in a proximal direction and resheath in a distal direction; and
    a static tube disposed within the reinforced outer sheath at a distal end of a handle of the delivery device, the static tube comprising a plurality of slits along a longitudinal length of the static tube, the slits being configured to receive a proximal portion of a stabilizing element so as to create a weaving of the stabilizing element into and out of the slits.

17. The delivery device of claim 16, wherein the proximal reinforced section comprises a braid.

18. The delivery device of claim 16, wherein the distal reinforced section comprises a coil.

19. The delivery device of claim 16, further comprising an overlapping section extending between the proximal reinforced section and the distal reinforced section, the overlapping section comprising a proximal portion of the coil affixed to a distal portion of the braid.

* * * * *